United States Patent
Kozak et al.

(12) 
(10) Patent No.: US 6,458,837 B1
(45) Date of Patent: Oct. 1, 2002

(54) LIPOPHILIC DIESTERS OF CHELATING AGENTS

(75) Inventors: Alexander Kozak, Rehovot; Israel Shapiro, Ramla, both of (IL)

(73) Assignee: D-Pharm Ltd., Rehovot (IL)

( * ) Notice: Subject to any disclaimer, the term of this patent is extended or adjusted under 35 U.S.C. 154(b) by 0 days.

(21) Appl. No.: 09/509,393

(22) PCT Filed: Sep. 27, 1998

(86) PCT No.: PCT/IL98/00468

§ 371 (c)(1),
(2), (4) Date: Mar. 27, 2000

(87) PCT Pub. No.: WO99/16741

PCT Pub. Date: Apr. 8, 1999

(30) Foreign Application Priority Data

Sep. 28, 1997 (IL) ................................................. 121844

(51) Int. Cl.[7] ......................... A61K 31/24; A01N 37/12; A01N 37/44

(52) U.S. Cl. ......................... 514/539; 514/532; 514/533; 514/534; 514/535; 514/539; 514/540; 514/826; 514/836; 514/886; 554/103; 554/104; 554/105; 554/107; 554/108; 564/463; 564/503; 564/504; 564/505; 564/509; 564/511; 568/579; 568/583; 568/589; 568/671; 568/672; 568/673

(58) Field of Search .......................... 554/103, 104, 554/105, 107, 108; 564/463, 503, 504, 505, 509, 511; 568/579, 583, 589, 671, 672, 673; 514/532, 533–35, 538–540, 826, 836, 886

(56) References Cited

U.S. PATENT DOCUMENTS

| | | | |
|---|---|---|---|
| 3,497,535 A | 2/1970 | Lennon | 260/398.5 |
| 3,751,440 A | 8/1973 | Spivack | 260/439 R |
| 4,500,627 A | 2/1985 | Naito et al. | 430/203 |
| 4,603,161 A | 7/1986 | Phillips et al. | 524/239 |
| 4,849,362 A | 7/1989 | DeMarinis et al. | 436/63 |
| 5,453,517 A | 9/1995 | Kuhn et al. | 549/227 |

FOREIGN PATENT DOCUMENTS

| | | | |
|---|---|---|---|
| JP | 58067652 | 4/1983 | |
| WO | 9408573 | 4/1994 | A61K/31/00 |
| WO | 9640292 | 12/1996 | A61K/51/00 |

OTHER PUBLICATIONS

Tsien, R. Y., "New Calcium Indicators and Buffers with High Selectivity Against Magnesium and Protons: Design, Synthesis, and Properties of Prototype Structures," Biochemistry, vol. 19, No. 11, May 27, 1980, pp. 2396–2404.

Stephen M. Karesh et al., "Biological Distributing of Chemical Analogs of Fatty Acids and Long Chain Hydrocarbons Containing a Strong Chelating Agent," J. of Pharmaceutical Sciences, vol. 66, No. 2, Feb. 1977, pp. 225–228.

*Primary Examiner*—Deborah D. Carr
(74) *Attorney, Agent, or Firm*—Davidson, Davidson & Kappel, LLC

(57) ABSTRACT

The invention discloses stable diesters of chelating agents of divalent metal ions, processes for their preparation and pharmaceutical compositions thereof. Most preferred compounds according to the present invention are stable lipophilic diesters comprising a covalent conjugate of a BAPTA and a pharmaceutically acceptable alcohol. The diesters are useful in a method for treating a condition or disease related to an excess of divalent metal ions, and in particular for the treatment of a condition or disease related to elevated levels of intracellular calcium ions, such as in brain or cardiac ischemia, stroke, epilepsy, Alzheimer's disease or cardiac arrhythmia and in open heart surgery.

41 Claims, 12 Drawing Sheets

LIPOPHILIC DIESTERS OF CHELATING AGENTS

This application is a 571 of PCT/IL98/00468 filed Sep. 29, 1998.

FIELD OF THE INVENTION

The present invention relates to lipophilic diesters of a chelating agent, to processes of synthesizing these agents, to pharmaceutical compositions thereof and to their use in treating a condition or disease related to abnormal levels of divalent metal ions, in particular to elevated levels of intracellular calcium ions. More particularly the invention relates to diesters of 1,2-bis(2 aminophenoxy)ethane-N,N,N',N'-tetraacetic acid denoted herein as BAPTA which are stable lipophilic derivatives of divalent metal ions chelator.

BACKGROUND OF THE INVENTION

Metal ions such as calcium, manganese, magnesium, copper, zinc and ferrous ions play a pivotal role in biological systems by regulating protein structure, enzyme activity and cellular signaling. Various diseases or pathological states including brain and cardiac ischemia, stroke, myocardial infarction, epilepsy, chronic neurodegenerative diseases such as Alzheimer's disease, Parkinson's disease and acute inflammation are all believed to be related to the phenomenon of abnormally elevated intracellular calcium levels. Other diseases associated with neuronal and muscular hyperactivity such as urinary incontinence, prostatic hypertrophy, muscular spasm, arterial hypertension, asthma, irritable bowel syndrome, have all been related to elevated levels of intracellular divalent ions such as calcium and zinc.

Intracellular calcium is an important determinant for cell death, irrespective of the initial insult sustained by the cell. It may be involved in cell death in lymphocyte and killer cell mediated damage of target cells, in organ damage during transplantation, and in other types of tissue damage including ischemic insults. Calcium channel blockers or cell membrane permeable forms of calcium chelators have been suggested to protect against tissue injury or to decrease tissue damage.

The cell damage occurring in ischernia may be secondary to the influx and/or intracellular release of $Ca^{2+}$ ions (Choi, Trends Neurosci., 1988, 11, 465–469; Siesjo and Smith, Arzneinittelforschung, 1991, 41, 288–292). Similarly, calcium influx appears to play an important role in the genesis of epileptic seizures. Although a significant portion of intracellular calcium arrives from intracellular stores, current research suggests that calcium entry blockers may have anticonvulsant activity (see e.g. Meyer, 1989, Brain Res. Rev 14, 227–243).

Accordingly, certain pharmacological strategies have been developed intending to prevent or treat this pathological accumulation of intracellular calcium, which may result from pathological release of calcium from intracellular deposits or by detrimental calcium influx into cells.

Drugs which are currently or potentially useful for treatment of calcium associated disorders include: (i) calcium channel blockers, (ii) drugs affecting calcium balance by modification of intracellular calcium storage sites, and (iii) intracellular calcium chelating agents. Calcium channel blockers used in clinical practice are represented by Verapamil, Nifedipine and Diltiazem. The major toxicities associated with the use of such compounds involve excessive vasodilation, negative inotropy, depression of the sinus nodal rate, and A-V nodal conduction disturbances. Drugs affecting calcium mobilization and/or sequestration, like calcium channel blockers, exhibit rather narrow specificity.

Among the highest affinity and most selective calcium chelators are various derivatives of 1,2-bis-(2-aminophenoxyethane)-N,N,N',N',-tetraacetic acid (BAPTA) which was originally described by Tsien (Biochem. 19, 2396, 1980). Various fluorescent and other reactive derivatives of BAPTA have been disclosed for example in U.S. Pat. Nos. 4,603,209, 4,849,362, 5,049,673 and 5,453,517. None of these disclosed derivatives is a stable diester of the chelator.

The use of calcium chelators for reducing injury to mammalian cells is disclosed in the International Publication No. WO 94/08573, which describes use of cell membrane permeable esters of calcium chelating agents as prodrugs for clinical requirements. Available cell membrane permeable chelators of $Ca^{++}$ and other divalent metal ions, include acetoxymethyl esters such as ethyleneglycol bis 2-aminoethyl ether N,N,N',N',tetra-acetic acid acetoxymethyl ester (EGTA-AM), ethylene diamine tetra-acetic acid acetoxymethyl ester (EDTA-AM) and 1,2-bis(2-aminophenoxy)ethane-N,N,N',N'-tetra-acetic acid acetoxymethyl ester (BAPTA-AM). These known complex molecules are prodrugs digested by ubiquitous esterases, consequently causing activation of the chelator in the intracellular space. Thus, the esterase-sensitivity of these compounds leads, under physiological conditions, to high circulating levels of free BAPTA and low efficacy of the drug at the target site. Accordingly, BAPTA-AM, for example, has to be used at relatively high therapeutic dosage that is associated with toxicity.

SUMMARY OF THE INVENTION

In accordance with one aspect of the present invention, there are provided novel stable lipophilic diesters of chelating agents. Thus, the invention provides a stable di-esterified carboxylic acid (a) with hydroxy compound (b), where (a) is a pharmaceutically acceptable chelating agent for divalent metal ions having the formula $(HOOC-CH_2-)_2-N-A-N-(-CH_2COOH)_2$ wherein A is saturated or unsaturated, aliphatic, aromatic or heterocyclic linking radical containing, in a direct chain link between the two depicted nitrogen atoms, 2–8 carbon atoms in a continuous chain which may be interrupted by 2–4 oxygen atoms, provided that the chain members directly connected to the two depicted nitrogen atoms are not oxygen atoms, and (b) is a pharmaceutically acceptable alcohol selected from the group of straight chain or branched, saturated or unsaturated alkyl, aminoalkyl and substituted or unsubstituted arylalkyl radicals; and pharmaceutically acceptable salts of said di-esterified carboxylic acids.

According to preferred embodiments of the present invention there are provided diesters of the chelating agents ethylene-1,2-diamine-N,N,N',N',-tetraacetic acid, ethylene-1,2-diol-bis-(2-aminoethyl ether)-N,N,N',N'-tetraacetic acid and in particular diesters of 1,2-bis-(2-aminophenoxy)ethane-N,N,N',N'-tetraacetic acid.

According to a more preferred embodiment of the invention, there are provided diesters of the general formula I:

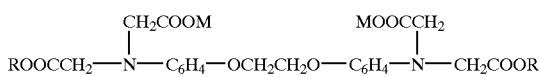

Formula 1 wherein the substituents on the aromatic rings are in the ortho position;

R is selected from the group consisting of $C_nH_{2n+1}$ (n=1–10), $C_nH_{2n+1}(OCH_2CH_2)_m$ (n=1–20, m=1–6), $(C_nH_{2n+1})_2N(CH_2)_m$ (n=1–6, m=1–6) and substituted or unsubstituted $ArCH_2$; and M denotes any physiologically acceptable cation.

Currently preferred compounds according to the invention are compounds of the general formula I wherein R is selected from the group consisting of: $C_2H_5$, $C_3H_7$, i-$C_3H_7$, $C_4H_9$, $C_7H_{15}$, $C_8H_{17}$, $CH_2C_6H_5$, $CH_3OCH_2CH_2$, $C_2H_5OCH_2CH_2$, $C_3H_7OCH_2CH_2$, $C_4H_9OCH_2CH_2$, $C_7H_{15}OCH_2CH_2$, $C_8H_{17}OCH_2CH_2$, $C_{10}H_{21}OCH_2CH_2$, $C_{16}H_{33}OCH_2CH_2$, $C_{18}H_{37}OCH_2CH_2$, $CH_3(OCH_2CH_2)_2$, $C_2H_5(OCH_2CH_2)_2$, $C_4H_9(OCH_2CH_2)_2$, $C_6H_{13}(OCH_2CH_2)_2$, $C_7H_{15}(OCH_2CH_2)_2$, $C_8H_{17}(OCH_2CH_2)_2$, $C_{10}H_{21}(OCH_2CH_2)_2$, $CH_3(OCH_2CH_2)_3$, $(CH_3)_2NCH_2CH_2$, $C_7H_{15}(OCH_2CH_2)_3$.

More preferred are compounds of the general formula I wherein R is selected from the group consisting of: $C_2H_5$, $C_3H_7$, $C_4H_9$, $C_7H_{15}$, $C_8H_{17}$, $C_8H_{17}OCH_2CH_2$, $C_{10}H_{21}OCH_2CH_2$, $C_{16}H_{33}OCH_2CH_2$, $C_{18}H_{37}OCH_2CH_2$, $C_8H_{17}(OCH_2CH_2)_2$, $C_{10}H_{21}(OCH_2CH_2)_2$.

For certain pharmaceutical embodiments according to the present invention, most preferred are compounds of the above-depicted general formula I wherein R is $C_8H_{17}$ or $C_8H_{17}OCH_2CH_2$.

In accordance with another aspect of the invention, there are provided pharmaceutical compositions comprising as an active ingredient a stable lipophilic diester of a chelating agent according to the invention and a pharmaceutically acceptable diluent or carrier. The pharmaceutical compositions may be in liquid or solid dosage forms and may be orally, parenterally or intranasally administered.

The lipophilic diesters of chelating agents according to the invention are useful in the treatment or prevention of metal ion-associated disorders, for example, disorders associated with abnormal levels of manganese, magnesium, copper, zinc, iron, cadmium, mercury, cobalt, and in particular calcium ions. Thus, in yet another aspect, the present invention provides a method for treating a disease or disorder related to an excess of divalent metal ions, comprising administering to an individual in need thereof a therapeutically effective amount of a stable lipophilic diester of a pharmaceutically acceptable chelating agent for divalent metal ions. In particular, the present invention provides a method for treating a disease or disorder related to an excess of intracellular $Ca^{++}$ ions, such as brain and cardiac ischemia, stroke, myocardial infarction, epilepsy, Alzheimer's disease, Parkinson's disease, acute inflammation, urinary incontinence, prostatic hypertrophy, muscular spasm, arterial hypertension, asthma and irritable bowel syndrome. Said method comprising administering to an individual in need thereof a therapeutically effective amount of a pharmaceutically acceptable diester of a chelating agent in accordance with the invention. The compounds of the invention may also be useful in medical treatments such as open heart surgery.

BRIEF DESCRIPTION OF THE DRAWINGS

The invention will be understood and appreciated more fully from the detailed description below, in conjunction with the drawings, in which.

DETAILED DESCRIPTION OF THE INVENTION

Figure 1A:
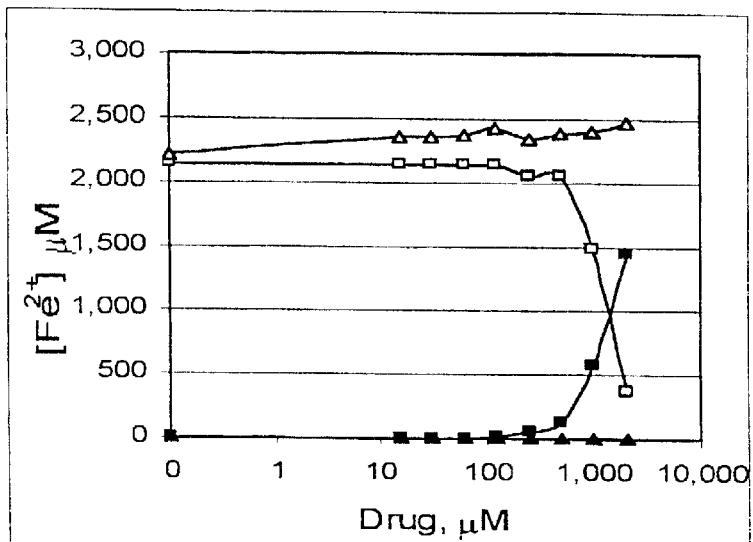
FIGS. 1A–C depict the concentration changes of three divalent metal ions (a) $Fe^{++}$, (b) $Zn^{++}$ and (c) $Ca^{++}$, in aqueous (open symbols) and octanol (filled symbols) solutions, in the presence of different concentrations of either dioctyl-ethylene glycol ester of BAPTA (DP-BAPTA-99, squares) or BAPTA (triangles).

According to the present invention, compounds are provided which are stable diesters of chelating agents of divalent metal ions. The divalent metal ions include, but are not limited to, manganese, magnesium, copper, cobalt, cadmium, mercury and plumbum, more preferably zinc and ferrous ions, and most preferably calcium ions.

In the specification and in the claims the term "chelating agent" denotes any molecule capable of chelating divalent metal ions as known in the art. The term "stable" denotes any molecule which is robust enough to be isolated in substantially pure form.

The diesters of the invention are lipophilic derivatives of chelating agents as may be measured by conventional methods including in terms of their increased octanol/water partition coefficients compared to the underivatized parent compounds.

According to one aspect of the invention is provided a stable di-esterified carboxylic acid (a) with hydroxy compound (b), where (a) is a pharmaceutically acceptable chelating agent for divalent metal ions having the formula (HOOC—CH$_2$—)$_2$—N—A—N—(—CH$_2$COOH)$_2$ wherein A is saturated or unsaturated, aliphatic, aromatic or heterocyclic linking radical containing, in a direct chain link between the two depicted nitrogen atoms, 2–8 carbon atoms in a continuous chain which may be interrupted by 2–4 oxygen atoms, provided that the chain members directly connected to the two depicted nitrogen atoms are not oxygen atoms, and (b) is a pharmaceutically acceptable alcohol selected from the group of straight chain or branched, saturated or unsaturated alkyl, aminoalkyl and substituted or unsubstituted arylalkyl radicals; and pharmaceutically acceptable salts of said di-esterified carboxylic acids.

In one embodiment of the invention, the linking radical A is selected from the group consisting of —(CH$_2$CH$_2$)$_m$— where m=1–4, in which 2–4 of the carbon atoms not attached to nitrogen may be replaced by oxygen atoms, and —CR=CR—O—CH$_2$CH$_2$—O—CR'=CR'—, where each of the pairs of radicals R—R and R'—R', together with the attached —C=C— moiety, complete an aromatic or heterocyclic ring containing 5 or 6 ring atoms, the ring completed by R—R being the same as or different from the ring completed by R'—R'.

In a particular embodiment the linking radical A may be selected from —CH$_2$CH$_2$— and —CH$_2$CH$_2$—O—CH$_2$CH$_2$—O—CH$_2$CH$_2$—; or it may be —CR=CR—O—CH$_2$CH$_2$—O—CR'=CR'—, where each of the pairs of radicals R—R and R'—R', together with the attached —C=C— moiety, complete an aromatic or heterocyclic ring which is selected from the group consisting of furan, thiophene, pyrrole, pyrazole, imidazole, 1,2,3-triazole, oxazole, isoxazole, 1,2,3-oxadiazole, 1,2,5-oxadiazole, thiazole, isothiazole, 1,2,3-thiadiazole, 1,2,5-thiadiazole, benzene, pyridine, pyridazine, pyrimidine, pyrazine, 1,2,3-triazine, 1,2,4-triazine, and 1,2-, 1,3- and 1,4-oxazines and -thiazines, the ring completed by R—R being the same as or different from the ring ompleted by R'—R'.

In a preferred embodiment the linking radical A is —CR=CR—O—CH$_2$CH$_2$—O—CR'=CR'—, where each of the pairs of radicals R—R and R'—R', together with the attached —C=C— moiety, completes the same or different rings selected from unsubstituted and substituted benzene rings, in which substituted benzene rings contain 1–4 substituents selected from the group consisting of saturated or unsaturated C$_{1-4}$-alkyl, saturated or unsaturated C$_{1-4}$-alkoxy, fluorine, chlorine, bromine, iodine and CF$_3$, or a single divalent substituent which is —O—(CH$_2$)$_n$—O— and n=1–3.

It is currently preferred that the calcium chelating agent incorporated in the drug is selected from ethylene-1,2-diamine-N,N,N',N'-tetra-acetic acid, ethylene-1,2-diol-bis-(2-aminoethyl ether)-N,N,N',N'-tetraacetic acid and 1,2-bis-(2-aminophenoxy)ethane-N,N,N',N'-tetraacetic acid.

Most preferred compounds according to the present invention are of general formula I:

Formula 1

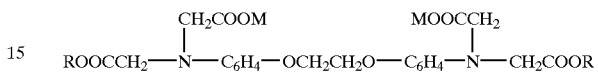

wherein the substituents on the aromatic rings are in the ortho position;

R is selected from the group consisting of C$_n$H$_{2n+1}$(n=1–10), C$_n$H$_{2n+1}$(OCH$_2$CH$_2$)$_m$(n=1–20, m=1–6), (C$_n$H$_{2n+1}$)$_2$N(CH$_2$)$_m$(n=1–6, m=1–6) and substituted or unsubstituted ArCH$_2$; and M denotes any physiologically acceptable cation.

In a particularly preferred embodiment, the diester of the invention is a compound of the general formula I as defined above wherein R is selected from the group consisting of C$_2$H$_5$, C$_3$H$_7$, i-C$_3$H$_7$, C$_4$H$_9$, C$_7$H$_{15}$, C$_8$H$_{17}$, CH$_2$C$_6$H$_5$, CH$_3$OCH$_2$CH$_2$, C$_2$H$_5$OCH$_2$CH$_2$, C$_3$H$_7$OCH$_2$CH$_2$, C$_4$H$_9$OCH$_2$CH$_2$, C$_7$H$_{15}$OCH$_2$CH$_2$, C$_8$H$_{17}$OCH$_2$CH$_2$, C$_{10}$H$_{21}$OCH$_2$CH$_2$, C$_{16}$H$_{33}$OCH$_2$CH$_2$, C$_{18}$H$_{37}$OCH$_2$CH$_2$, CH$_3$(OCH$_2$CH$_2$)$_2$, C$_2$H$_5$(OCH$_2$CH$_2$)$_2$, C$_4$H$_9$(OCH$_2$CH$_2$)$_2$, C$_6$H$_{13}$(OCH$_2$CH$_2$)$_2$, C$_7$H$_{15}$(OCH$_2$CH$_2$)$_2$, C$_8$H$_{17}$(OCH$_2$CH$_2$)$_2$, C$_{10}$H$_{21}$(OCH$_2$CH$_2$)$_2$, CH$_3$(OCH$_2$CH$_2$)$_3$, (CH$_3$)$_2$NCH$_2$CH$_2$, and C$_7$H$_{15}$(OCH$_2$CH$_2$)$_3$.

More preferably R is selected from the group consisting of: C$_2$H$_5$, C$_3$H$_7$, C$_4$H$_9$, C$_7$H$_{15}$, C$_8$H$_{17}$, C$_8$H$_{17}$OCH$_2$CH$_2$, C$_{10}$H$_{21}$OCH$_2$CH$_2$, C$_{16}$H$_{33}$OCH$_2$CH$_2$, C$_{18}$H$_{37}$OCH$_2$CH$_2$, C$_8$H$_{17}$(OCH$_2$CH$_2$)$_2$, C$_{10}$H$_{21}$(OCH$_2$CH$_2$)$_2$.

Most preferably R is C$_8$H$_{17}$ or C$_8$H$_{17}$OCH$_2$CH$_2$.

In another preferred embodiment, the compositions according to the invention comprise a conjugate of a pharmaceutically acceptable chelating agent of divalent metal ions and a monoalkyl or a monoalkyl ether of ethylene glycols. Currently preferred ethylene glycols include mono-, di- and tri-ethylene glycols. It is also possible to use tetra-, penta- or hexa-ethylene glycols, but these compounds would require special reaction conditions due to their hygroscopic properties.

Unexpectedly, it has now been found, that di-esters of 1,2-bis-(2-aminophenoxy)ethane-N,N,N',N'-tetraacetic acid (herein designated as BAPTA-diester or DP-BAPTA) have greatly improved therapeutic applications compared to other derivatives of this calcium chelator.

It is clear that the lipophilicity of the novel BAPTA-diesters is greater than that of the parent compound, and their enhanced activity may be due to the fact that they are retained within the plasma membrane of the cells or other cell membrane compartments or in their vicinity and thereby exert their enhanced capacity to modulate cellular functions. It is possible that these diesters of chelating agents are targeted to the vicinity of the cell membrane. Irrespective of the exact mechanism of action it is disclosed that these diesters have an enhanced therapeutic profile.

According to the present invention it is shown that the lipophilic nature of the diesters is dependent on the residues attached to the carboxylic groups of the BAPTA molecule as well as on the counter-ions on the non esterified carboxylic groups (respectively denoted by R and M in the above-depicted formula I).

The lipophilicity of a di-ester compound greatly depends on the length of the aliphatic chains in R, and dramatically increases as the number of carbons in R increases up to 7 atoms. For aliphatic chains longer than $C_7$ the increase per each carbon added is smaller. In general, mono- di- or tri-ethylene glycols at the R position increase the lipophilicity of the compound. Hence, the choice of the different esterified R-groups may serve for fine-tuning of the biological activity of the designed compounds in accordance with the invention. The chosen counter-ion should also be considered for the lipophilicity of a particular di-ester. For example, as shown in Table 1, a more elevated octanol partition was observed for Ca-salt versus Na-salts.

The choice of the preferred alcohol and counter-ion that are appropriate for any given composition is dependent on the intended therapeutic use of the conjugate, and may be optimized by the artisan in accordance with the principles of the invention.

Persons skilled in the art will appreciate in what manner the concept of the invention may be applied to conditions and diseases which are related to abnormal levels of divalent metal ions, particularly calcium ions, so that the compositions according to the invention will comprise a diester of an active compound which is a metal ion-chelator but which will possess optimized pharmacological activity.

Many events (e.g. cytotoxic chemicals, physical stimuli and infective agents) causing damage of the cell membrane can trigger a cascade leading ultimately to a condition which mimics ischemic damage (Robbins et al, Pathological Basis for Disease, 1984, p. 10, W. B. Saunders Co.). The present invention will potentially be of use for protecting cells in these circumstances, by introduction of a divalent metal ions-chelator either intracellularly or into the plasma membrane or its vicinity.

The compounds of the invention may be useful in open heart surgery and for the treatment of medical conditions associated with increased levels of divalent metal ions, in particular calcium. These conditions may include, but are not limited to, brain and cardiac ischemia, stroke, myocardial infarction, epilepsy, chronic neurodegenerative diseases such as Alzheimer's disease, Parkinson's disease and acute inflammation as well as diseases associated with neuronal and muscular hyperactivity such as urinary incontinence, prostatic hypertrophy, muscular spasm, arterial hypertension, asthma and irritable bowel syndrome.

Various diesters according to the present invention were tested in experimental models of disorders associated with abnormal intracellular calcium levels. These experimental models included in-vitro and in-vivo system models of ischemia, cardiac arrythmia and epilepsy. BAPTA-diesters were shown to have pronounced protective activities in all these model systems.

The biological protective effects of the tested BAPTA-diesters of the invention were followed, in vitro, by monitoring parameters of cell function, enzymatic activities and survival following various insults such as glutamate toxicity and anoxia-induced neuronal cell death and ouabain-induced toxicity in cardiomyocytes.

The animal model systems of global forebrain ischemia induced in Mongolian Gerbils and epilepsy induced in Wistar rats represented in-vivo model systems.

Different diesters of BAPTA synthesized in our laboratory were proven to be especially effective as neuroprotective, anti-epileptic and cardioprotective compounds.

Neuroprotective Effects of BAPTA-diesters

BAPTA-diesters according to the invention were protective against glutamate toxicity and anoxia-induced cell death in cultured cortical neurons. The protective effect of the drug was evident both when the DP-BAPTA was added one hour before and up to at least one hour after the glutamate or anoxia insult period.

Ischemia Model

Global forebrain ischemia was induced in Mongolian Gerbils by bilateral common carotid artery occlusion. As a result brain damage was evident as judged from microscopic morphological data (histopathology analysis), altered cellular functions (NSE enzymatic activity) and whole animal performance (survival data).

Both dioctyl-BAPTA (DP-BAPTA-60) and Di(octyl-ethylene glycol)-BAPTA (DP-BAPTA-99) were effective in preventing the neuronal damage. The tested BAPTA-diesters extended the animal survival time by 2–3 folds.

It should be understood that the advantageous protective effects of BAPTA-diesters may be manifested in protecting against both focal and global brain ischemic damages.

Epilepsy Model

Epilepsies are a group of disorders characterized by chronic, recurrent, paroxymal changes in neurologic function caused by abnormalities in the electrical activity of the brain. The neurologic dysfunction episodes are called seizures, and are classified as partial or focal seizures, generalized seizures and status epilepticus. Among the major causes of epilepsy in humans are genetic predisposition, head trauma, brain tumors, cerebrovascular acidents and metabolic disturbances.

Epileptic episodes cause a major discomfort and aggravation in everyday life of the affected individuals and in many cases may be life-threatening and fatal. The most commonly used anti-epileptic drugs have been available for the last 20–30 years and all have their own limitations associated with problems of toxicity. Even following all the currently known anti-epileptic drugs and treatments, including surgery, does not provide complete prevention of seizure in a large percentage of the epileptic patients. The problem is exacerbated in patients that develop status epilepticus, which has around 30% mortality rate. Therefore, a safe and effective medicine with minimal side effects is of great need.

The animal model system used in this study for evaluating the protective effects of BAPTA-diesters was the well established experimental epilepsy in rats induced by pilocarpine (Turski W. A., E. A. Cavalhiero, M. Schwarz, S. J. Czuczwar, Z. Kleinrok and L. Turski (1983), Limbic seizures produced by pilocarpine in rats: Behavioral, Electroencephalographic and Neuropathological study. Behavioral Brain Research 9, 315–335).

Di(octyl-ethylene glycol)-BAPTA (DP-BAPTA-99) was capable of preventing generalized seizures and status epilepticus in the animal model system, as well as reducing mortality.

Cardioprotective Effects

Ventricular fibrillation (VF) is the most dangerous complication of myocardial infraction and cardiac surgery. It is successfully treated with the help of the cardioverter-defibrillator. Nevertheless, during electrical shock, there is risk of damage to the bypass and other kinds of transplants. Thus, a pharmacological approach to resolving the problem of VF in the field of cardiac surgery is for preferable. However, clinical pharmacology has no satisfactory drug for this purpose, because most of the known antiarrhythmic drugs enhance defibrillator energy requirements. A pharmacological approach is preferable for the treatment of the functional atrio-ventricular block connected with ischemia.

Diethyl-BAPTA (DP-BAPTA-23) was shown to abolish a delayed after depolarization in cultured cardiomyocytes that underwent ouabain toxicity episode. Thus, it may by useful in clinics for: 1) prophylaxis of VF or ventricular tachyarrhythmias (VT) and 2) treatment of altered conductivity. Many antiarrhythmic drugs have been successfully used for the above mentioned purposes. However, each of them has some undesired side-effect(s): proarrhythmic action, hypotension, negative inotropic effects. The mechanism of action of diesters of BAPTA is unknown for the present. However, it has no phenomenological analogy among conventional antiarrhythmic drugs. None of the known antifibrillatory drugs are capable of improving cardiac conductivity. These drawbacks of the known antifibrillatory drugs indicate an unmet medical need which shows the utility of diesters of BAPTA, as a new class of antifibrillatory drug, which may be especially useful in thoracic surgery.

It should be appreciated that BAPTA diesters, in several of the tested model systems, were shown to exert their therapeutic effects in both curative and preventive modes, thus may be administered either before or after the insult for prophylactic and healing purposes.

Accordingly, the BAPTA-diesters drugs of the present invention may be useful in treating or preventing a variety of pathological processes related to an excess of divalent metal ions, in particular excess of intracellular calcium ions. Such pathological processes as, for example, those induced in traumatic events such as brain injuries, stroke, ischemia and infraction or in chronic diseases such as epilepsy, Parkinson's disease and Alzheimer's disease. In addition, other diseases involving calcium dependent hyperactivity or ionic imbalance, such as acute inflammation, urinary incontinence, prostatic hypertrophy, muscular spasm, arterial hypertension, asthma and irritable bowel syndrome, may all benefit from treatment with the BAPTA-diesters drugs. The drugs may also be applied in sustaining maintenance of close to normal ion homeostasis during planned operations such as open heart and bypass surgeries.

Pharmaceutical compositions comprising as an active ingredient the diesters of chelating agents will contain in addition any pharmaceutically acceptable diluents or carriers as are known in the art. These compositions may be formulated into any suitable formulation including but not limited to solutions, suspensions, aerosols,micelles, emulsions, microemulsions, tablets, and the like, as will be required for the appropriate route of administration.

Any suitable route of administration is encompassed by the invention including, but not limited to, oral, intravenous, intramuscular, subcutaneous, inhalation, intranasal, rectal or other known routes. In preferred embodiments, the pharmaceutical compositions of the invention are administered intravenously, orally, or intramuscularly. The dose ranges for the administration of the compositions of the present invention are those large enough to produced the desired protective effect. The dosage administered will be depended upon the age, sex, health, weight of the recipient, kind of concurrent treatment, if any, frequency of treatment and the nature of the effect desired. Dosage regimen and means of administration will be determined by the attending physician or other person skilled in the art.

BAPTA-AM, which is a known compound, has been shown to have an effective cell protective activity in various pathological processes in which elevated calcium levels are implicated (Tymianski et al., Neuron 11, 221–235, 1993; Tymianski et al., J. Cerebral Blood Flow and Metabolism, 14, 911–923, 1994; Abdel-Hamid and Tymianski, J.Neuroscience, 17, 3538–3553). However, uncontrolled intervention in calcium homeostatis causes significant safety problems and clearly limits potential clinical applications. The novel diesters disclosed herein are more selective in their action, in that they do not appear to influence the intracellular calcium homeostasis and are therefore safer than the previously known derivatives of BAPTA.

EXAMPLES

A. Chemical Examples

Example 1

Synthesis of BAPTA Diesters of Alkyl and Salts Therof

The synthesis of disodium or calcium salts of diesters of 1,2-bis(2-aminophenoxy)ethane-N,N,N',N'-tetraacetic acid (BAPTA) was carried out in three steps as follows:.

Step 1. Preparation of an Anhydride of BAPTA

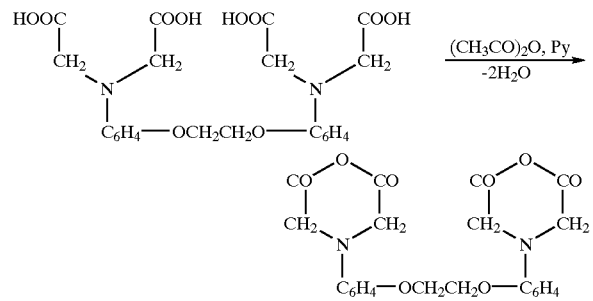

Step 2. Preparation of BAPTA Diester

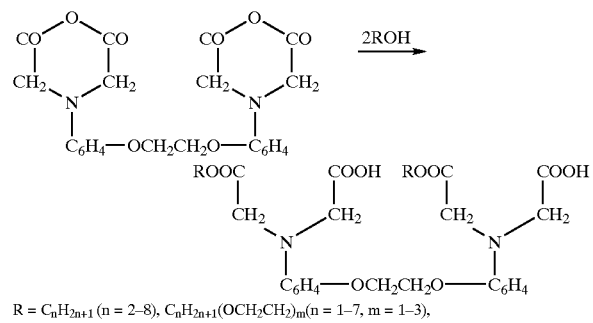

$R = C_nH_{2n+1}$ (n = 2–8), $C_nH_{2n+1}(OCH_2CH_2)_m$(n = 1–7, m = 1–3), $(C_nH_{2n+1})_2N(CH_2)_m$(n = 1–6, m = 1–6), $ArCH_2$

According to additional preferred embodiments, advantageously R can also be $C_nH_{2n+1}$ wherein n=1–10 and $C_nH_{2n+1}(OCH_2CH_2)_m$ wherein n=1–20, m=1–6.

Step 3 Preparation of Disodium or Calcium Salt of the Diester of BAPTA

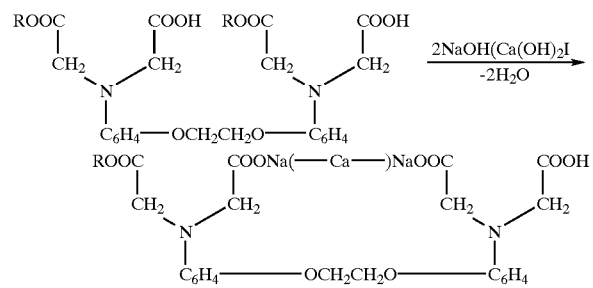

Step 1. Preparation of BAPTA anhydride

BAPTA (24 gr., 0.05 mol), pyridine (8 gr., 0.1 mol) and acetic anhydride (95 ml, 1.0 mol) are introduced into a round-bottom single-neck flask (500 ml), equipped with a reverse condenser (water cooling) and magnetic stirrer. The reaction mixture is heated at 90° C. for 5 hours with vigorous stirring by magnetic stirrer. The temperature is then decreased to 50° C. and heating is continued at this temperature for 10 hours longer. At the end of the 10-hour period the reaction mixture is cooled to room temperature and the precipitate is extracted by filtration. The precipitate is then washed four times with ethyl acetate (50 ml each wash) and twice with ether (60ml each wash). The precipitate is dried under vacuum at 50° C. for 6–8 hours. The product is a BAPTA anhydride. Yield 80% (17.6 g.). White solid. M.p. 148–149° C.

Analyses: TLC. The compound decomposed in the course of analysis.

$^1$H NMR ($C_6D_5NO_2$), δ(ppm): 4.40 (s, 8H), 4.47 (s, 4H) and 6.85–7.01 (m, 8H).

IR: 1762.9 cm$^{-1}$ (s), 1820.7 cm$^{-1}$ (s).

Elemental. $C_{22}H_{20}O_8N_2$. Calculated: C, 60.00%; H, 4.54%; N, 6.36%. Found: C, 59.60%; H, 4.66%; N, 6.20%.

Step 2. Preparation of alkyl or aryl diester of BAPTA

The BAPTA anhydride of step 1 (10 g, 0.023 Mol) and corresponding absolute alcohol (300 ml) are introduced, under argon atmosphere, into a round-bottom single-neck flask, equipped with reverse condenser and magnetic stirrer. The mixture is heated in an oil bath at 90° C. (for methyl and ethyl diesters at 70° C.) with vigorous stirring. After 6 hours about half of the alcohol is distilled from the reaction mixture (high molecular alcohols are distilled under vacuum). The obtained mixture is cooled to 0° C. and kept at this temperature for 5–8 hours. The precipitate is separated from the solution by filtration (glass filter N4) under vacuum and is washed 3–4 times with about 40 ml of ethanol, followed by three washes (100 ml each) of ethyl acetate and finally with three washes (150 ml each) of diethyl ether. The product is dried under vacuum for 8 hours.

The chemical/physical specifications of synthesized diesters of BAPTA are presented hereinbelow:

Ethyl diester of BAPTA. Yield 90% (11 g.). White powder. M.p. 161–162° C. TLC analysis. Silica gel 60 on aluminum sheet. Eluent is mixture of chloroform with methanol and water (80:20:1.5 v/v). For indication the chromatogram is sprayed by the indicator spray and then is charred at 350–400° C. Composition of indicator spray is 4-methoxybenzaldehyde (10 ml), ethanol (200 ml), 98% $H_2SO_4$ (10 ml) and glacial acetic acid (2 ml). One spot. $R_f$ 0.3.

$^1$H NMR ($CD_3OD$). δ(ppm): 1.05–1.11 (t, 6H), 3.91–4.00 (dd, 4H), 4.05 (s, 4H), 4.14 (s,4H), 4.27 (s, 4H), 6.83–6.96 (m, 8H).

Elemental. $C_{26}H_{32}O_{10}N_2$. Calculated: C, 58.64%; H, 6.03%; N, 5.26%. Found: 58.00%; H, 6.00%; N, 5.09%.

Propyl diester of BAPTA. Yield 90% (11.5 g.). White powder. M.p. 187° C. TLC analysis. Conditions of the analyses of diethyl and dipropyl esters of BAPTA are analogous. One spot. $R_f$ 0.35.

$^1$H NMR [$(CD_3)_2SO$], δ (ppm): 0.71–0.77 (t, 6H), 1.38–1.47 (m, 4H), 3.80–3.85 (t, 4H), 4.00 (s, 4H), 4.13 (s, 4H), 4.20 (s, 4H), 6.70–6.96 (m, 8H).

Elemental. $C_{28}H_{36}O_{10}N_2$. Calculated: C, 60.00%; H, 6.43%; N, 5.00%. Found: C, 60.25%; H, 6.77%; H, 5.08%.

Iso-propyl diester of BAPTA. Yield 80% (10.2 g.). White powder. M.p. 181–182° C. TLC analysis. Silica gel 60 $F_{254}$ on aluminum sheet. Eluent: chloroform:methanol (65:30, v/v). For indication the chromatogram is sprayed by the indicator spray and then is charred at 350–400° C. The composition of indicator spray is 4-methoxybenzaldehyde (10 ml), ethanol (200 ml), 98% sulfuric acid (10 ml) and glacial acetic acid (2 ml). One spot. $R_f$ 0.72.

$^1$H NMR [$(CD_3)_2SO$], δ (ppm): 1.07–1.09 (d, 12H), 4.00 (s, 4H), 4.08 (s, 4H), 4.22 (s, 4H), 4.78–4.85 (m, 2H), 6.71–6.98 (m, 8H).

Elemental analysis. $C_{28}H_{36}O_{10}N_2$. Calculated: C, 60.00%; H, 6.43%; N, 5.00%. Found: 59.78%; H, 6.50%; N, 5.00%.

Butyl diester of BAPTA. Yield 90% (12.1 g.). White powder. M.p. 183° C. TLC analysis. Conditions of analyses of diethyl and dibutyl esters of BAPTA are analogous. One spot. $R_f$ 0.42.

$^1$H NMR [$(CD_3)_2SO$]. δ (ppm): 0.74–0.80 (t,6H), 1.09–1.18 (m, 4H), 1.33–1.39 (m, 4H), 3.80–3.86 (t, 4H), 3.98 (s,4H), 4.10 (s, 4H), 4.17 (s, 4H), 6.69–6.92 (m, 8H).

Elemental. $C_{30}H_{40}O_{10}N_2$. Calculated: C, 61.22%; H, 6.80%; N, 4.76%. Found: C, 61.54%; H, 7.10%; 5.03%.

Heptyl diester of BAPTA. Yield 70% (10.8 g.). White powder. M.p. 146–147° C. TLC analysis. Conditions of analysis of ethyl and heptyl diesters of BAPTA are analogous. One spot. $R_f$ 0.50.

$^1$H NMR [$(CD_3)_2SO$]. δ (ppm): 0.79–0.84 (t, 6H), 1.08–1.17 (broad s, 16H), 1.34–1.43 (m, 4H), 3.79–3.87 (t, 4H), 3.98 (s, 4H), 4.13 (s, 4H), 4.17 (s, 4H), 6.67–6.92 (m, 8H).

Elemental: $C_{36}H_{52}O_{10}N_2$. Calculated: C, 64.29%; H, 7.74%; N, 4.16%. Found: C, 64.37%; H, 7.82%; N, 3.88%.

Octyl diester of BAPTA. Yield 70% (11.3 g.). White powder. M.p.155° C. TLC analysis. Conditions of analyses of diethyl and dioctyl esters of BAPTA are analogous. One spot. $R_f$ 0.55.

$^1$H NMR [$(CD_3)_2SO$], δ (ppm): 0.81–0.86 (t, 6H), 1.19–1.23 (broad s, 20H), 1.29–1.34 (m, 4H), 3.83–3.87 (m, 4H), 3.98 (s, 4H), 4.11 (s, 4H), 4.19 (s, 4H), 6.80–6.84 (m, 8H).

Elemental: $C_{38}H_{56}O_{10}N_2$. Calculated: C, 65.14%; H, 8.00%; N, 4.00%. Found: C, 64.91%; H, 8.20%; N, 3.76%.

Benzyl diester of BAPTA. Yield 70% (10.6 g.). White powder. M.p.161–163° C. TLC analysis. Conditions of analysis of ethyl and benzyl diester of BAPTA are analogous. One spot. $R_f$ 0.64 (Benzyl diester is plotted on TLC plate in solution in dimethylformamide).

$^1$H NMR [$(CD_3)_2SO$], δ (ppm): 4.02 (s, 4H), 4.18–4.19 (d, 8H), 4.97 (s, 4H), 6.73–6.94 (m, 8H), 7.22–7.32 (m, 10H).

Elemental analysis. $C_{36}H_{36}O_{10}N_2$. Calculated: C, 65.85%; H, 5.49%; N, 4.27%. Found: 65.56%; 5.83%; N, 4.12%.

2-(Dimethylamino)ethyl diester of BAPTA. Yield 70% (9.95 g.). White powder. M.p.126–127° C. TLC analysis. Silica gel 60 $F_{254}$ on aluminum sheet. Eluent: chloroform:methanol:water 60:40:2 v/v. One spot. $R_f$ 0.2.

$^1$H NMR ($CDCl_3$), δ (ppm): 2.57 (s, 12H), 2.60–2.63 (t, 4H), 3.60 (s, 4H), 3.75–3.78 (t, 4H), 4.06 (s, 4H), 0.11 (s, 4H), 6.68–6.85 (m, 8H).

Elemental analysis. $C_{30}H_{42}O_{10}N_4$. Calculated: C, 58.25%; H, 6.80%; N, 9.06%. Found: C, 57.94%; H, 6.90%; N, 8.97%.

Step 3a. Preparation of sodium salts of diesters of BAPTA

Corresponding alkyl diester of BAPTA (0.019 Mol) is introduced into an Erlenmeyer flask (500 ml), equipped with a magnetic stirrer. About 250 ml of a mixture of methanol with water (1:1 v/v) is added to the ester. This mixture is vigorously stirred, because the ester is not dissolved in the solution. A concentrated solution of $NaHCO_3$ (0.038 mol, 3.19 g.) or concentrated solution of MeONa (0.038 mol) in water is added to the stirring mixture, and after 5–8 hours the mixture becomes transparent. This indicates that the alkyl diester is converted into disodium salt. Methanol and water are evaporated under vacuum. The obtained salt is dried by azeotropic distillation with ethanol and diethyl ether. Finally, the salt is dried under vacuum (5–6 mm Hg) for 8 hours.

Ethyl diester of BAPTA, disodium salt. White powder. Yield 95% (10.4 g.). Elemental analysis. $C_{26}H_{30}O_{10}N_2Na_2$. Calculated: C, 54.16%; H, 5.21%; N, 4.86%; Na, 7.98%. Found: 54.10%; H, 5.27%; N, 4.65%; Na, 8.10%.

Propyl diester of BAPTA, disodium salt. White powder. Yield 95% (10.9 g.). Elemental analysis. $C_{28}H_{36}O_{10}N_2Na_2$. Calculated: 55.63%; H, 5.63%; N, 4.63%; Na, 7.61%. Found: 54.76%; H, 6.13%; N, 4.46%; Na, 6.73%.

Butyl diester of BAPTA, disodium salt. White powder. Yield 95% (11.2 g.). Elemental analysis. $C_{30}H_{38}O_{10}N_2Na_2$. Calculated: C, 56.96%; H, 6.01%; N, 4.43%; Na, 7.28%. Found: C, 56.50%; H, 6.00%; N, 4.20%; Na, 7.30%.

Heptyl diester of BAPTA, disodium salt. White powder. Yield 90% (10.3 g.). Elemental analysis. $C_{36}H_{50}O_{10}N_2Na_2$. Calculated: C, 60.33%; H, 6.98%; N, 3.91%; Na, 6.42%. Found: C, 59.88%; H, 7.49%; N, 4.12%; Na, 6.76%.

Octyl diester of BAPTA, disodium salt. White powder. Yield 90% (15.7 g.). Elemental analysis. $C_{38}H_{54}O_{10}N_2Na_2$. Calculated: C, 61.29%; H, 7.26%; N, 3.76%; Na, 6.16%. Found: C, 60.90%; H, 7.81%; N, 3.26%; Na, 6.52%.

Step 3b. Preparation of calcium salts of diesters of BAPTA

The corresponding diester of BAPTA (1 g.) is dissolved in 1 L of mixture of ethanol with water (70:30 v/v). The equivalent molal of $Ca(OH)_2$ is added to this solution. The obtained mixture is stirred by magnetic stirrer at room temperature for 24 hours. Then for the salts of ethyl, propyl and butyl diesters of BAPTA the solution is filtrated through Whatmann paper N1 and evaporated under vacuum (20–30 mm Hg) to dry. The precipitate is washed three times by diethyl ether (each portion is 100 ml) and dried under vacuum (2–3 mm Hg) at room temperature for 6 hours.

For the calcium salts of heptyl and octyl diesters of BAPTA the ethanol solution is evaporated to dry. The precipitate is dissolved in 0.8 L of ethanol. The obtained mixture is filtrated through Whatmann paper N1 and then ethanol is evaporated under vacuum (20–25 mm Hg). The precipitate is washed three times by diethyl ether (each portion is 100 ml) and dried under vacuum (2–3 mm Hg) at room temperature for 6–7 hours.

Ethyl diester of BAPTA, calcium salt. White powder. Yield 90% (0.96 g.). $C_{26}H_{30}N_2O_{10}Ca$. Calculated: C, 54.70%; H, 5.26%; N, 4.91%; Ca, 7.01%. Found: C, 54.32%; H, 5.40%; N, 4.81%; Ca, 6.81%.

Propyl diester of BAPTA, calcium salt. White powder. Yield 90% (0.98 g.). $C_{28}H_{34}N_2O_{10}Ca$. Calculated: C, 56.19%; H, 5.68%; N, 4.68%; Ca, 6.69%. Found: C, 56.22%; H, 5.88%; N, 4.51%; Ca, 6.51%.

Butyl diester of BAPTA, calcium salt. White powder. Yield 90% (0.90 g.). $C_{30}H_{38}N_2O_{10}Ca$. Calculated: C, 57.50%; H, 6.07%; N, 4.47%; Ca, 6.39%. Found: C, 57.18%; H, 6.24%; N, 4.28%; Ca, 6.11%.

Heptyl diester of BAPTA, calcium salt. White powder. Yield 80% (0.85 g.). $C_{36}H_{50}N_2O_{10}Ca$. Calculated: C, 61.71%; H, 7.14%; N, 4.00%; Ca, 5.71%. Found: C, 61.44%; H, 7.24%; N, 4.18%; Ca, 6.31%.

Octyl diester of BAPTA, calcium salt. White powder. Yield 80% (0.83 g.). $C_{38}H_{54}N_2O_{10}Ca$. Calculated: C, 61.79%; H, 7.32%; N, 3.79%; Ca, 5.42%. Found: C, 61.94%; H, 7.14%; N, 4.00%; Ca, 5.31%.

Example 2
Synthesis of BAPTA Diesters of Alkyl Ether of Mono-, Di- and Triethylene Glycol and Salts Thereof The procedure for synthesis of these salts is a four-step process similar to the procedure for preparation of the salts of the alkyl diesters of BAPTA.

Step 1. Preparation of BAPTA anhydride

This first step of obtaining a BAPTA anhydride is identical to step 1 in the procedure for synthesizing the alkyl diesters of BAPTA as described above in Example 1.

Step 2. Synthesis of monoalkyl ethers of mono-, di- and triethylene glycol

The synthesis of monoalkyl ethers of mono-, di- and triethylene glycol is carried out according to following scheme:

$$H(OCH_2CH_2)_mOH + Na \rightarrow H(OCH_2CH_2)_mONa + 1/2 H_2 H(OCH_2CH_2)_mONa + C_nH_{2n+1}Br \rightarrow H(OCH_2CH_2)_mOC_nH_{2n+1} + NaBr$$

m=1–3, n=5–18

About 0.8–0.9 g. of sodium (cut into small pieces where the diameter of each piece is 5–8 mm) are introduced, under argon atmosphere, into a double-neck round-bottom flask (250 ml), equipped with a reverse condenser and magnetic stirrer. Ethylene glycol (35 ml, 0.62 Mol) is added to the sodium, also under argon, and the flask is heated in oil bath at 70° C. with vigorous stirring. When most of the sodium is dissolved the rest of the sodium (typical quantity of sodium is 3.9 g., 0.17 Mol) is added piece by piece to the reaction mixture. It should be noted that sodium dissolution is accompanied by an increase in the temperature of the reaction mixture together with the increased reaction rate. In order to avoid explosion, it is necessary to add sodium slowly so that the reaction is well controlled. After all of the sodium is dissolved a drop funnel with the solution of the corresponding alkyl bromide (21.5 g., 0.12 Mol) in tetrahydrofuran (60 ml) is added to the reaction flask. The solution from the drop funnel is introduced drop-by-drop into the reaction flask. The temperature of the reaction mixture is kept at 70° C. Almost at once the precipitate of sodium bromide appears and increases in quantity in the course of the reaction. After 16 hours the reaction mixture is cooled to room temperature and about 150 ml of water is added to the organic solution. The product is extracted by two portions (40 ml each) of ethyl acetate. The combined ethyl acetate solution is washed with water and dried by sodium sulfate. The yellow solution of the product in ethyl acetate is discolored by heating with activated carbon. The colorless solution is separated from the carbon by filtration and the solvent is evaporated. The obtained product is distilled under vacuum and analyzed for its physical and chemical characteristics.

Monoheptyl ether of ethylene glycol. Colorless liquid. B.p.95° C./1 mm Hg. Yield 70%(13.4 g.).

TLC analysis. Silica gel 60 $F_{254}$ on aluminum sheet. Eluent: ethyl acetate:n-hexane, 2:1 v/v. Indicator: 4-methoxybenzaldehyde (10 ml), ethanol (200 ml), 98% sulfuric acid (10 ml) and glacial acetic acid (2 ml). For indication the chromatogram is sprayed by the indicator spray and then it is charred at 350° C. One spot. $R_f$ 0.8.

$^1$H NMR (CDCl$_3$), δ (ppm): 0.84–0.90 (t, 3H), 1.27–1.33 (broad s, 8H), 1.55–1.61 (m, 2H), 2.25–2.30 (t, 1H, signal of OH-group, its position variable), 3.43–3.54 (m, 4H), 3.69–3.75 (m, 2H).

Heptyl ether of diethylene glycol. Colorless liquid. B.p. 100° C./1 mm Hg. Yield 70% (17.1 g.).

TLC analysis. Conditions of analyses of heptyl ether of mono- and diethylene glycol are analogous. One spot. $R_f$ 0.4.

$^1$H NMR (CDCl$_3$), δ (ppm): 0.84–0.90 (t, 3H), 1.27–1.32 (broad s, 8H), 1.55–1.61 (m, 2H), 2,71(t, 1H, signal of OH-group), 3.45–3.48 (t, 2H), 3.58–3.75 (m, 8H).

Heptyl ether of triethylene glycol. Colorless liquid. B.p. 107° C./1 mm Hg. Yield 70% (20.8 g.).

TLC analysis. Conditions of analyses of monoheptyl ether of mono- and triethylene glycol are analogous. One spot. $R_f$ 0.3.

$^1$H NMR (CDCl$_3$), δ (ppm): 0.84–0.90 (t,3H), 1.26–1.29 (broad s, 8H), 1.54–1.57 (m, 2H), 2.72 (t, 1H, signal of OH-group), 3.41–3.47 (t,2H), 3.58–3.74 (m, 12H).

Octyl monoethylene glycol. Colorless liquid. B.p. 60° C./0.5 mm Hg. Yield 85%.

TLC analysis. Conditions of analyses of dioctyl ether of ethylene glycol are the same as above. One spot. $R_f$ 0.7.

$^1$H NMR (CDCl$_3$), δ (ppm): 0.83–0.89 (t,3H), 1.25–1.27 (broad s, 10H), 1.54–1.57 (m, 2H), 2.39 (t, 1H), 3.41–3.52 (m,4H), 3.67–3.73 (m, 4H).

Step 3. Synthesis of BAPTA diesters of monoalkyl ethers of mono-, di- and triethylene glycol The BAPTA anhydride of step 1 (1.5 g., 0.0034 Mol) and the corresponding monoalkyl ether of mono-, di- or triethylene glycol of step 2 (10–12 ml) are introduced, under argon atmosphere, into a round-bottom single-neck flask (50 ml), equipped with a reverse condenser and a magnetic stirrer. The mixture is heated in an oil bath at 115–120° C. with vigorous stirring. After 1–1.5 hours the mixture becomes transparent. Heating is continued for another 1.5 hours, till the reaction is completed. The flask is then cooled to room temperature and about 100 ml of petroleum ether (b.p. 60–80° C.) is added. The formed precipitate is extracted by centrifugation and washed three times with petroleum ether (40 ml each wash). The solid product is dried under vacuum for 5 hours and analyzed to verify the product characteristics, as exemplified for the following compounds:

BAPTA diester of methylethylene glycol. White solid. M.p.151–152° C. Yield 90% (1.81 g).

TLC analysis. Silica gel 60 F$_{254}$ on aluminum sheet. Eluent is chloroform:methanol (1:1 v/v). For indication the chromatogram is sprayed by the indicator spray and then is charred at 100–150° C. Composition of indicator spray is 4-methoxybenzaldehyde (10 ml), ethanol (200 ml), 98% sulfuric acid (10 ml) and glacial acetic acid (2 ml). One spot. $R_f$ 0.14.

$^1$H NMR (CD$_3$OD), δ (ppm): 3.33 (s, 6H), 3.47–3.51 (t, 4H), 3.66 (s, 4H), 3.85 (s, 4H), 4.02–4.06 (t, 4H), 4.35 (s, 4H), 7.02–7.11 (m, 8H).

Elemental analysis. C$_{28}$H$_{36}$O$_{12}$N$_2$. Calculated: C, 56.76%; H, 6.08%; N, 4.73%. Found: C, 56.38%; H, 6.39%; N, 4.72%.

BAPTA diester of heptylethylene glycol. White solid. M.p. 111–112° C. Yield 90% (2.32 g.).

TLC analysis. Conditions of TLC analysis of BAPTA diester of methylethylene glycol and BAPTA diester of heptylethylene glycol are the same. One spot. $R_f$ 0.4.

$^1$H NMR [(CD$_3$)$_2$SO], δ (ppm): 0.81–0.86 (t,6H), 1.22 (broad s, 16H), 1,42 (m, 4 h), 3.27–3.32 (m, 4H), 3.37–3.40 (m, 4H), 3.96–3.99 (m, 8H), 4.12 (s, 2H), 4.19 (s, 2H), 6.73–6.92 (m, 8H).

Elemental analyses. C$_{40}$H$_{60}$O$_{12}$N$_2$. Calculated: C, 63.16%; H, 7.90%; N, 3.68%. Found: C, 63.30%; H, 8.44%; N, 3.76%.

BAPTA diester of octylethylene glycol. White solid. M.p. 121–122° C., Yield 80% (1.4 gr). TLC analysis. Silica gel 60 on aluminum sheet. Eluent is chloroform:methanol (1:1, v/v). For indication the chromatogram is sprayed by the indicator spray and then is charred at 100–150° C. Composition of indicator spray is 4-methoxybenzaldehyde (10 ml), ethanol (200 ml), 98% sulfuric acid (10 ml), and glacial acetic acid (2 ml). One spot. $R_f$ 0.45.

$^1$H NMR (CDCl$_3$), δ (ppm) 0,84–0.89 (t, 6H), 1.26 (broad s, 20H), 1.51–1.57 (m, 4H), 3.37–3.42 (t, 4H), 3.53–3.56 (m, 4H), 3.96 (s, 4H), 4.03 (s, 4H), 4.17–4.21 (m, 4H), 4.37 (s, 4H), 6.87–6.94 (m, 4H), 7.03–7.09 (m,4H).

Elemental analysis. C$_{42}$H$_{64}$N$_2$O$_{12}$. Calculated: C, 63.96%; H, 8.12%; N, 3.55%. Found: C, 63.57%; H, 8.11%; N, 3.53%.

BAPTA diester of heptyldiethylene glycol. White solid. M.p.95–96° C. Yield 85% (2.5 g.).

TLC analysis. Conditions of analysis of BAPTA diester of methylethylene and BAPTA diester heptyldiethylene glycol are the same. One spot. $R_f$ 0.40.

$^1$H NMR [(CD$_3$)$_2$SO], δ (ppm): 0.81–0.86 (t, 6H), 1.23 (broad s, 16H), 1.45 (m, 4H), 3.30–3.35 (m, 8H), 3.40–3.46 (m, 12H), 3.97–3.99 (m, 8H), 4.13 (s, 4H), 4.19 (s, 4H), 6.74–6.92 (m, 8H), 12.37 (s, 2H).

Elemental. C$_{44}$H$_{68}$O$_{14}$N$_2$. Calculated: C, 62.26%; H, 8.02%; N, 3.30%. Found: C, 6.47%; H, 8.42%; N, 3.40%.

BAPTA ester of heptyltriethylene glycol. White solid. M.p.63–65° C. Yield 85% (2.7 g.).

TLC analysis. Conditions of analysis of BAPTA diester of heptyltriethylene glycol and BAPTA diester of methylethylene glycol are the same. One spot. $R_f$ 0.40.

$^1$H NMR [(CD$_3$)$_2$SO], δ (ppm): 0.81–0.87 (t, 6H), 1.23 (broad s, 16H), 1.45 (m, 4H), 3.31–3.36 (m, 4H), 3.42–3.48 (m, 20H), 3.97–3.99 (m,8H), 4.13 (s, 4H), 4.19 (s, 4H), 6.74–6.92 (m, 8H), 12.38 (s, 2H).

Step 4a. Preparation of disodium salt of BAPTA diesters of monoalkyl ethers of mono-, di- or triethylene glycol.

The corresponding BAPTA diester of monoalkyl ether of mono-, di- or triethylene glycol (0.0025 Mol) is dissolved in methanol (around 10 ml of alcohol is necessary for dissolving 1.0 g. of BAPTA diester) and the obtained solution is introduced into an Erlenmeyer flask (50 ml), equipped with a magnetic stirrer. A water solution of sodium bicarbonate (0.005 Mol in 2 ml) is added to a methanol solution of the BAPTA diester and the mixture is stirred for 2 hours at room temperature. The solvent is then evaporated under vacuum (30 mm Hg). The obtained precipitate is dried three times by azeotropic distillation with ethanol and two times with diethyl ether. Finally, the obtained product is washed with hexane and is dried under vacuum.

BAPTA diester of methylmonoethylene glycol, disodium salt. White solid. Hygroscopic. Yield 95% (1.5 g.).

Elemental analysis. C$_{28}$H$_{34}$O$_{12}$N$_2$Na$_2$. Calculated: C, 52.80%; H, 5.35%; N, 4.40%; Na, 7.23%. Found: 52.20%; H, 5.59%; N, 4.49%; Na, 7.30%.

BAPTA diester of heptylmonoethylene glycol, disodium salt. White solid. Hygroscopic. Yield 95% (1.9 g.).

Elemental analysis. C$_{40}$H$_{58}$O$_{12}$N$_2$Na$_2$. Calculated: C, 59.70%; H, 7.21%; N, 3.48%; Na, 5.72%. Found: C, 59.60%; N, 7.75%; N, 3.51%; Na, 5.51%.

BAPTA diester of heptyldiethylene glycol, disodium salt. White solid. Hygroscopic. Yield 95% (2.1 g.).

Elemental analysis. C$_{44}$H$_{66}$O$_{14}$N$_2$Na$_2$. Calculated: C, 59.19%; H, 7.40%; N, 3.14%; Na, 5.16%. Found: C, 58.55%; H, 7.43%; N, 3.46%; Na, 5.49%.

BAPTA diester of heptyltriethylene glycol, disodium salt. White wax. Very hygroscopic. Yield 90% (2.2 g.).

Elemental analysis. C$_{48}$H$_{74}$O$_{16}$N$_2$Na$_2$. Calculated: C, 58.77%; H, 7.55%; N, 2.86%; Na, 4.69%. Found: C, 57.98%; H, 8.03%; N, 2.94%; Na, 4.64%.

BAPTA diester of octylethylene glycol, disodium salt. White solid. Yield 80%. TLC analysis. Silica gel 60 on aluminum sheet. Eluent is chloroform:methanol (1:1, v/v). For indication the chromatogram is sprayed by the indicator spray and then is charred at 100–150° C. Composition of indicator spray is 4-methoxybenzaldehyde (10 ml), ethanol (200 ml), 98% sulfuric acid (10 ml), and glacial acetic acid (2 ml). One spot. $R_f$ 0.45.

1H NMR (CDCl₃), δ (ppm) 0,84–0.89 (t, 6H), 1.26 (broad s, 20H), 1.51–1.57 (m, 4H), 3.37–3.42 (t, 4H), 3.53–3.56 (m, 4H), 3.96 (s, 4H), 4.03 (s, 4H), 4.17–4.21 (m, 4H), 4.37 (s, 4H), 6.87–6.94 (m, 4H), 7.03–7.09 (m,4H).

Elemental analysis. $C_{42}H_{64}N_2O_{12}$. Calculated: C, 63.96%; H, 8.12%; N, 3.55%. Found: C, 63.57%; H, 8.11%; N, 3.53%.

Step 4b. Preparation of calcium salt of BAPTA diesters of monoalkyl ethers of mono-, di- or triethylene glycol.

The corresponding monoalkyl ether of mono-, di- or triethylene glycol diester of BAPTA (0.0025 Mol) is dissolved into 250 ml methanol. About 3–5 ml of water is added to this solution. The obtained solution is introduced into an Erlenmeyer flask (300 ml), equipped with a magnetic stirrer. The powder of $CaH_2$ (0.0025 Mol) is added to this solution with vigorous stirring. The stirring is continued for 3 hours at room temperature. After 3 hours the mixture is filtered through paper filter (Whatman N1) and the obtained solution is evaporated under vacuum (10–15 mm Hg). The precipitate is dried three times by azeotropic distillation with ethanol (each portion is 25–30 ml) and two times with diethyl ether. Finally, the product is washed with hexane and it is dried under vacuum (5 mm Hg) for 5 hours at room temperature.

Methylmonoethylene glycol diester of BAPTA, calcium salt. White powder Yield 90% (1.42 g.). $C_{28}H_{34}N_2O_{12}Ca$. Calculated: C, 53.33%; H, 5.40%; N, 4.44%; Ca, 6.35%. Found: C, 53.74%; H, 5.78%; N, 4.43%; Ca, 5.90%.

Heptylmonoethylene glycol diester of BAPTA, calcium salt. White powder. Yield 90% (1.79 g.). $C_{40}H_{58}N_2O_{12}Ca$. Calculated: C, 60.15%; H, 7.27%; N, 3.51%; Ca, 5.01%. Found: C, 60.32%; H, 7.63%; N, 3.54%; Ca, 4.59%.

Octylmonoethylene glycol diester of BAPTA, calcium salt. White powder. Yield 90% (1.81 g.). $C_{42}H_{62}N_2O_{12}Ca$. Calculated: C, 61.01%; H, 7.50%; N, 3.38%; Ca, 4.84%. Found: C, 61.00%; H, 7.82%; N, 3.54%; Ca, 4.88%.

Heptyldiethylene glycol diester of BAPTA, calcium salt. White solid. Yield 80% (1.77 g.). $C_{44}H_{66}N_2O_{14}Ca$. Calculated: C, 59.59%; H, 7.44%; N, 3.16%; Ca, 4.51%. Found: C, 59.61%; H, 7.79%; N, 3.15%; Ca, 4.04%.

Methyltriethylene glycol diester of BAPTA, calcium salt. White solid. Yield 80% (1.61 g.). $C_{36}H_{50}N_2O_{16}Ca$. Calculated: C, 53.60%; H, 6.20%; N, 3.47%; Ca, 4.96%. Found: C, 53.95%; H, 6.33%; N, 3.20%; Ca, 4.73%.

Example 3
In vitro Lipophilicity Measurements of BAPTA Diesters Salts

The lipophilicity values of several BAPTA diesters salts of the invention were studied by comparing the solubility of these compounds in organic versus aqueous solutions. Octanol and physiological saline were used, respectively, as the organic and aqueous solutions. The partition coefficient ($P_c$), i.e the distribution ratio between the organic and the aqueous phases were determined for several specific BAPTA diesters salts of the general formula I:

Formula 1

wherein the substituents on the aromatic rings are in the ortho position,

R is $C_nH_{2n+1}$ (n=2–8) or $C_nH_{2n+1}(OCH_2CH_2)_m$ (m=1–3, n=1–18) and M represents $Na^+$ or $Ca^{++}$ as indicated.

The results, presented as the calculated $LogP_c$, are shown in Table 1.

TABLE 1

Octanol-saline partition coefficients ($P_c$) of BAPTA diesters

| | $LogP_c$[a] | |
| R in formula I | M = $Na^+$ | M = $Ca^{++}$ |
| --- | --- | --- |
| [b] | −3.3[c] | −1.71[d] |
| $C_2H_5$ | −1.61 | −1.33 |
| $C_3H_7$ | −0.63 | −0.51 |
| $C_4H_9$ | −0.01 | 0.32 |
| $C_7H_{15}$ | 0.82 | 0.76 |
| $C_8H_{17}$ | 0.85 | 0.79 |
| $CH_3OCH_2CH_2$ | −2.27 | −1.85 |
| $C_2H_5OCH_2CH_2$ | −1.41 | −0.99 |
| $C_3H_7OCH_2CH_2$ | −0.81 | −0.48 |
| $C_4H_9OCH_2CH_2$ | −0.06 | 0.14 |
| $C_7H_{15}OCH_2CH_2$ | 1.34 | 1.00 |
| $C_8H_{17}OCH_2CH_2$ | 0.80 | 1.10 |
| $C_{10}H_{21}OCH_2CH_2$ | 1.90 | 1.50 |
| $C_{16}H_{33}OCH_2CH_2$ | 1.67 | [e] |
| $C_{18}H_{37}OCH_2CH_2$ | 1.50 | [e] |
| $CH_3(OCH_2CH_2)_2$ | −1.82 | −1.18 |
| $C_2H_5(OCH_2CH_2)_2$ | −1.20 | −0.73 |
| $C_4H_9(OCH_2CH_2)_2$ | −0.29 | 0.03 |
| $C_6H_{13}(OCH_2CH_2)_2$ | 0.83 | 0.95 |
| $C_7H_{15}(OCH_2CH_2)_2$ | 1.30 | 0.95 |
| $C_8H_{17}(OCH_2CH_2)_2$ | [e] | 1.20 |
| $C_{10}H_{21}(OCH_2CH_2)_2$ | 1.25 | 1.02 |
| $CH_3(OCH_2CH_2)_3$ | −1.93 | −1.00 |
| $C_7H_{15}(OCH_2CH_2)_3$ | [e] | [e] |

[a] At 26° C. [b] BAPTA. [c] Tetrasodium salt. [d] Dicalcium salt. [e] Not determined It will be appreciated that the majority of the novel diesters of BAPTA are significantly more lipophilic than the native BAPTA. Interestingly, the partition coefficients are also influenced by the choice of counter-ions. Generally, the calcium salts of BAPTA diesters are more lipophilic than their corresponding sodium salts.

Example 4
In vitro Effects of BAPTA Diesters on the Water/Octanol Distribution of $Ca^{++}$, $Fe^{++}$ and $Zn^{++}$ ions The chelating activities of the novel BAPTA diesters of the invention in aqueous and hydrophobic environments were examined and are demonstrated here by the effect of the dioctyl-ethylene glycol ester of BAPTA (DP-BAPTA 99, disodium salt) on three different divalent metal ions: $Fe^{++}$, $Zn^{++}$ and $Ca^{++}$.

The hydrophilic/hydrophobic system used in this set of experiments consisted of 15 ml octanol and 15 ml saline pH=6.5. DP-BAPTA 99 was dissolved in the octanol solution before this phase was mixed with the saline. The DP-BAPTA concentration in the different experiments varied from $2.1 \times 10^{-6}$ to $5.5 \times 10^{-4}$ M/L in the experiments with $Ca^{2+}$ and from $5.4 \times 10^{-6}$ to $1.4 \times 10^{-3}$ M/L in the experiments with either $Zn^{2+}$ or $Fe^{2+}$, as indicated for each point in FIGS. 1A–C. The corresponding metal ions were added in the aqueous solution as chlorides at the following concentrations: $FeCl_2$ $2 \times 10^{-3}$ M/L, $ZnCl_2$ $10^{-4}$ M/L, $CaCl_2$ $2 \times 10^{-3}$ M/L.

The octanol and buffer phases were mixed and vortexed for 1 hr at room temperature, followed by centrifugation at 4000 rpm, 10 min in order to separate the mixture to the two phases.

Different analytical procedures were employed for water and octanol samples: i) Water samples were analyzed versus ICP standards from Merk. Ca and Zn were determined in tested solutions by inductively coupled plasma atomic emission spectrometry. An ICP-AES, model "Spectroflame Modula E" from Spectro, Kleve, Germany was used, with a standard cross flow nebulizer and fixed EOP torch. The power level was 1.2 kW, coolant flow—15 l/min, auxilliary flow 0.5 l/min and nebulizer flow—0.5 l/min. ii) Octanol samples, 2-ml each, in a glass tube, were transferred to a heating block. Octanol evaporation was achieved by combination of heating at 150° C. and continuous flushing with nitrogen. The residue was dissolved in 2 ml of concentrated nitric acid and heated for one hour at 120° C. The tubes were then allowed to cool to room temperature before deionized water was added to final volume of 10 ml.

It was shown that the dioctyl-ethylene glycol ester of BAPTA is 10,000 fold more lipophilic than the sodium salt of the parent molecule BAPTA, and is preferentially soluble in the organic solvent, represented here by octanol.

Figure 1B:
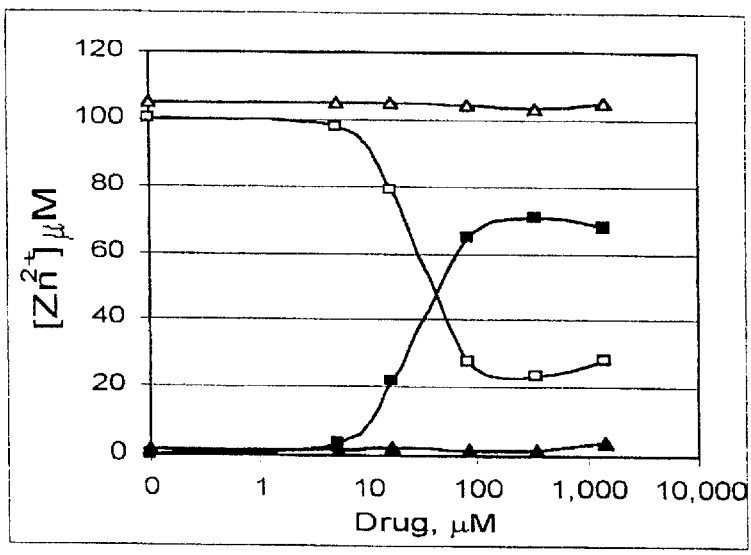
Figure 1C:
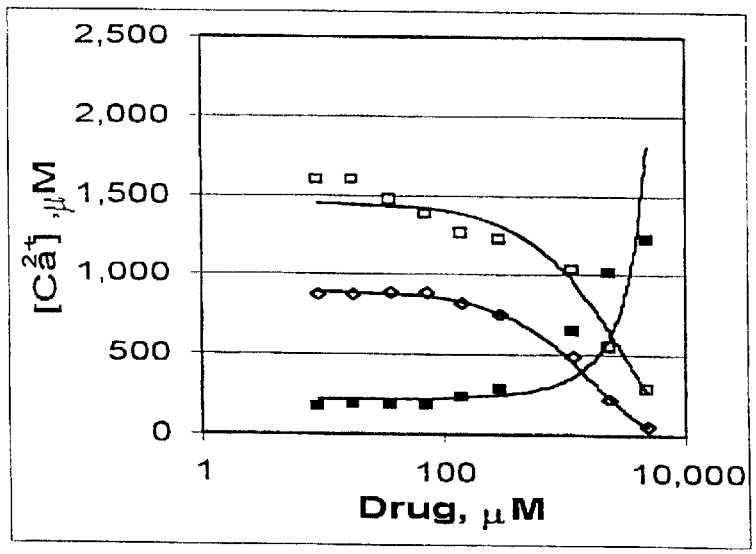

Furthermore, as shown in FIGS. 1A–C, the BAPTA diester mediates transfer of metal ions from water to octanol and accumulation of these ions in the organic phase, while BAPTA does not. This preferential chelating effect of the BAPTA diester is evident in transferring of $Zn^{++}$ ions from water to octanol at a drug concentration as low as 10 µM and at 250–500 µM drug for the corresponding transfer of $Ca^{++}$ and $Fe^{++}$ ions.

B. Biological Evaluation of Diesters of BAPTA

The novel diesters of chelating agents according to the invention were tested in various biological model systems for their protective effects on cells or organs in culture undergoing insults involving abnormal calcium levels. Results of experiments conducted in-vitro (tissue culture cells; brain homogenates) and in-vivo (Mongolian Gerbils and Wistar rats) are presented hereinbelow.

Example 5

Effects of BAPTA Diesters on Intracellular $Ca^{++}$ Concentration (in vitro Studies)

The chelating effects of two different BAPTA-diesters on intracellular $Ca^{++}$ concentration was examined in vitro in cultured neuronal cells of rat hippocampus, and were followed by fluorescence recordings.

Cell culture. Primary dissociated cultures of rat hippocampus were prepared from E19 fetuses and grown on 13 mm cover glasses for 104 weeks. In brief, cells were plated in DMEM containing 10% horse serum and 10% fetal calf serum, which was replaced, after 1 week, with DMEM containing 10% horse serum. Glia proliferation was blocked by incubation with 5-fluoro-2'-deoxyuridine for 3 d, starting 5 d after plating. For $Ca^{2+}{}_i$ imaging, cover glasses were washed with recording medium and incubated with 3 µm Fluo-3/AM (Molecular probes) in the presence of 0.2% (w/v) pluronic acid (F127) for 1–1.5 hr in shaking at room temperature. Cultures were then washed for at least 1 hr in the recording medium and were used during the next 1–3 hr.

Solutions and drugs. The recording medium contained: 129 mM NaCl, 4 mM KCl, 1 mM $MgCl_2$, 2 mM $CaCl_2$, 4.2 mM glucose and 10 mM HEPES. pH was adjusted to 7.4 with NaOH and osmolarity to 320 mOsm by addition of sucrose. The BAPTA-diesters diethyl-BAPTA (DP-BAPTA 23) or dioctyl-ethylene glycol-BAPTA (DP-BAPTA 99), both disodium salts, were prepared in the recording medium from frozen stocks before use. The BAPTA-diester, as indicated in each experiment, was loaded, at final concentration of 0.1 mM, in a pressure pipette with a tip diameter of 2 µm, placed approximately 50 µm from the cell. The drugs were applied through the pipette with a pressure pulse of 0.5–5 sec duration.

Imaging. After loading of the dye, Fluo-3/AM (Molecular probes), the glass coverslips were placed in a confocal laser scanning microscope (Leica, Heildelberg, Germany) and superfused with the recording medium including 1 µM tetrodotoxin (TTX) at the rate of 3–5 ml/min at room temperature. The confocal laser scanning microscope is equipped with an argon-ion laser for excitation at a wavelength of 488 nm. Laser light was reduced to 1–3% of nominal intensity to avoid photodynamic damage. Images of 256×256 pixels were taken with a 63×water immersion objective. A complete three-dimensional reconstruction of the cell was made from 15–20 successive 0.5–1.0 µm optical sections taken through the cell when need. Fluorescence intensity was quantified using Leica analysis software and Adobe Photoshop (Adobe Systems). Changes in Fluo-3 fluorescence were standardized by dividing the net fluorescence by the pretreated fluorescence ($\Delta F/F$).

Figure 2:
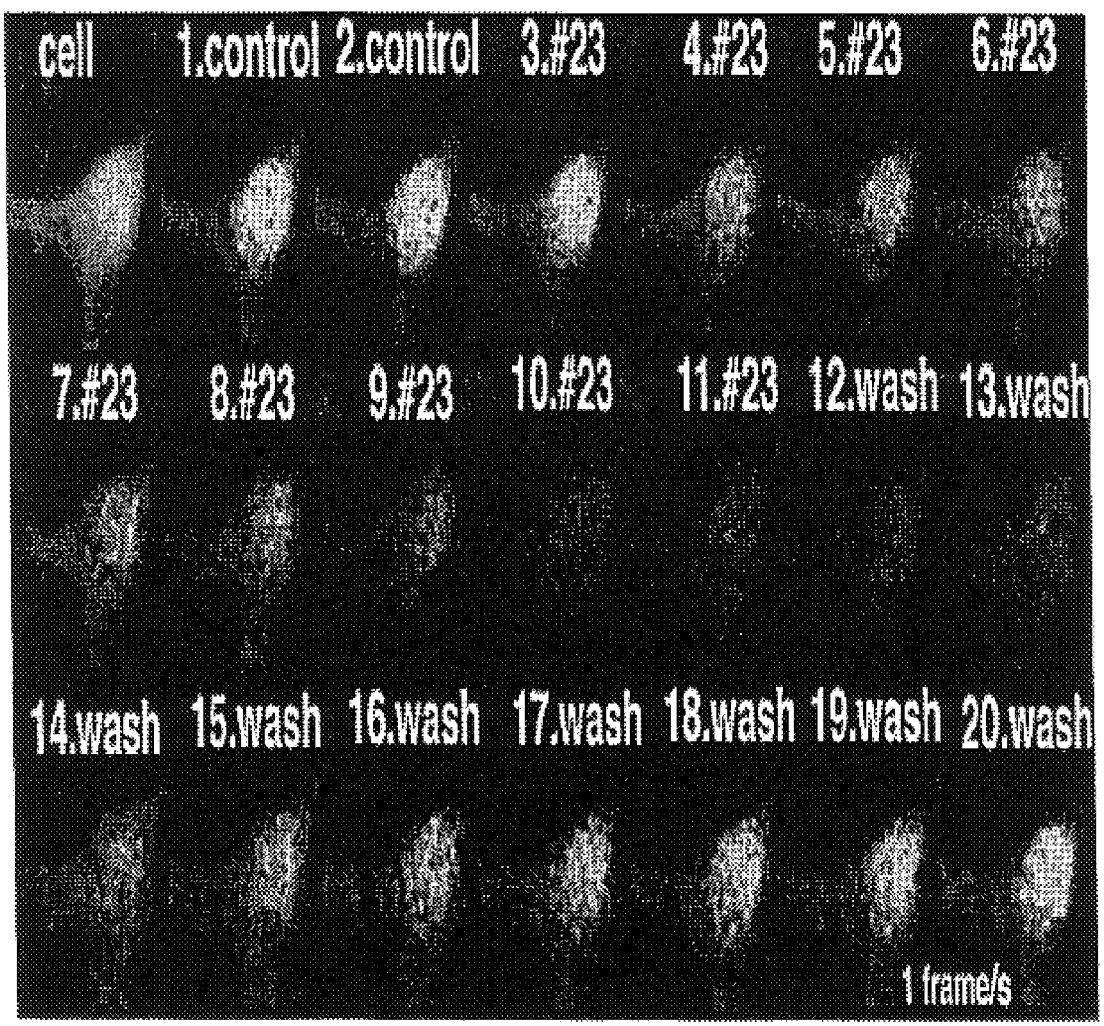
FIG. 2 depicts the effect of diethyl ester of BAPTA (DP-BAPTA-23) on intracellular $Ca^{++}$ concentration in cultured hippocampal neurons, as monitored by fluorescence of the dye Fluo-3/AM.

Hippocampal neuronal cells grown in DMEM medium containing 2.4 mM $Ca^{++}$, were either treated with the vehicle, i.e. the recording medium, (FIG. 2, frames 1,2) or treated with DP-BAPTA 23 (FIG. 2, frames 3 to 11). The addition of the drug (1 mM in 9 sec. pulse) induced a decrease in the intracellular calcium levels, reflected by reduction in fluorescence recorded in the treated cells. This temporary reduction in $Ca^{++}$ concentration, was followed by complete recovery within 7–8 Sec after the drug was washed off the cells (see FIG. 2, frames 12 to 20). Shorter applications of the same amount of drug induced shorter and smaller reductions of fluorescence in the same cell (data not shown).

It is important to note that same concentrations of the tetra-sodium salt of the parent drug, $BAPTA-Na_4$, which is cell-membrane non-permeable drug, promote only insignificant increase in intracellular $Ca^{2+}$ while applied onto the surface of cultured neurons of rat hippocampus (data not shown).

Figure 3:
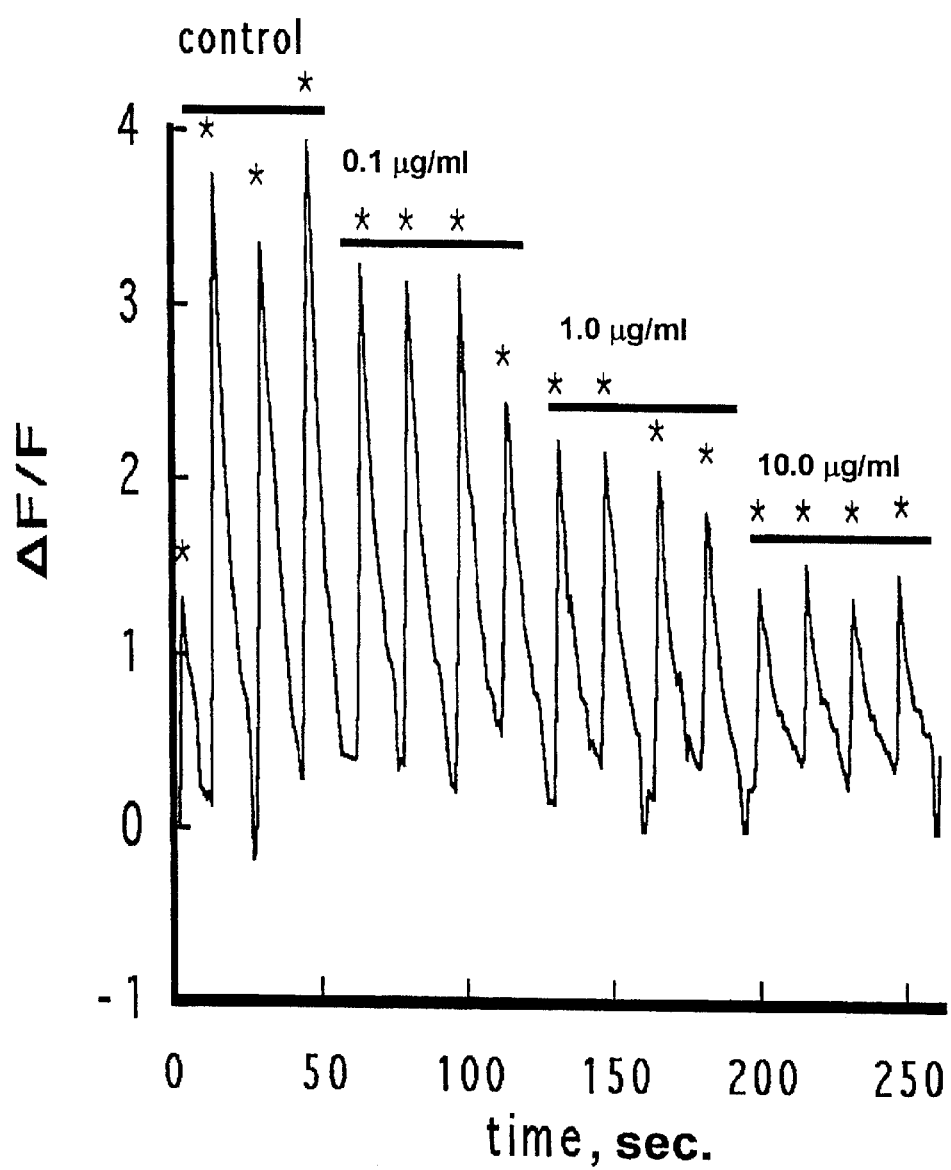
FIG. 3 depicts a graph of fluorescence changes ($\Delta$ F/F) of the dye Fluo-3/AM, averaged from five cultured hippocampal neurons, representing the effect of different concentrations of DP-BAPTA-99 (0.1 µg/ml, 1 µg/ml and 10 µg/ml) on potassium-induced increase in intracellular $Ca^{++}$ concentration. Asterisks (*) represent $K^+$ pulse.

In FIG. 3 is demonstrated the effect of BAPTA diesters on potassium-induced increase in intracellular $Ca^{2+}$ concentrations.

Hippocampal neuronal cells were grown as described above, and were exposed to 40 millisecond $K^+$ pulses (applied from a pipette containing 100 MM KCl) at time points as indicated by asterisks (*). Under the control conditions, each such $K^+$ pulse evoked an 3–4 fold increase in the intracellular $Ca^{2+}$ concentration, recorded as a transient increase in the fluorescence signal.

The cells were then perfused with 0.1, 1.0 or 10.0 µg/ml of dioctyl-ethylene glycol-BAPTA (DP-BAPTA 99) for 5 minutes before each recording period. The results depicted in FIG. 3 are the graphical presentations of the fluorescence changes averaged from five individual hippocampal neuronal cells.

As shown in FIG. 3, the BAPTA diester attenuates potassium-induced increase in intracellular calcium ion concentration and executes this effect in a concentration-dependent manner.

Example 6

Effects of BAPTA-diesters on Na/K-ATPase Activity

Fernandes et. al. (Neurochem Int. 28:497–500, 1996) studied the activity of the enzyme Na/K-ATPase in rat hippocampus, during experimental epilepsy induced by pilocarpine injection. It was found, according to this study, that the enzyme activity decreased during the acute and silent periods and increased (though not to the normal levels) during the chronic phase of epilepsy. A possible conclusion from these results may be that changes in Na/K-ATPase activity could be involved in the appearance of spontaneous and recurrent seizures following brain damage induced by pilocarpine injection.

Pilocarpine-induced seizures are considered to be a model for several types of human epilepsies and development of such. It is proposed that the decreased activity of the enzyme Na/K-ATPase, resulting in increased extracellular $K^+$ levels, can be a contributory factor to the epileptic condition and its development.

Thus, the effects of BAPTA-diesters on Na/K-ATPase activity were examined in mouse brain homogenates treated with different concentrations of diethyl-BAPTA (DP-BAPTA 27, disodium salt). The BAPTA-diester tested concentrations ranged from $10^{-7}$ to $10^2$ μg/ml.

Preparation of mouse brain homoganate. Male CD-1 mice (10 to 21 days of age) were sacrificed by rapid decapitation. The skull was opened, the brains removed and cut into two. The cortex was isolated, put into sodium Ringer's buffer, washed three times with ice cold PBS and kept on ice. The brain tissue was homogenized using a Polytron at 14000 rpm for 4×30 seconds, on ice. The homogenization buffer contained: 250 mM Sucrose; 1 mM EGTA; 20 mM HEPES-Tris, pH 7.4, and the protease inhibitor PMSF.

The homogenate was span down in a Sorval refrigerated centrifuge at 27000 g for 30 minutes. The membrane fraction was collected and re-suspended in the homogenization buffer. Fresh DP-BAPTA 27, was diluted for each experiment from 1 mg/ml stock solution, and was added into the ATPase reaction medium at final concentrations as indicated.

Na/K-ATPase assay. Na/K ATPase was measured as described before (Norby J, G. Coupled (1988) Assay of the $Na^+$—$K^+$ ATPase Activity. Methods in Enzymology. 156: 116–119) in the absence and presence of the Na/K-ATPase inhibitor, ouabain (3 mM). The Protein content was determined using the Bio Rad-Bradford assay as previously described (Bradford, M. (1978) Protein assay. Ann. Biochem. 72: 248–257.).

Figure 4:
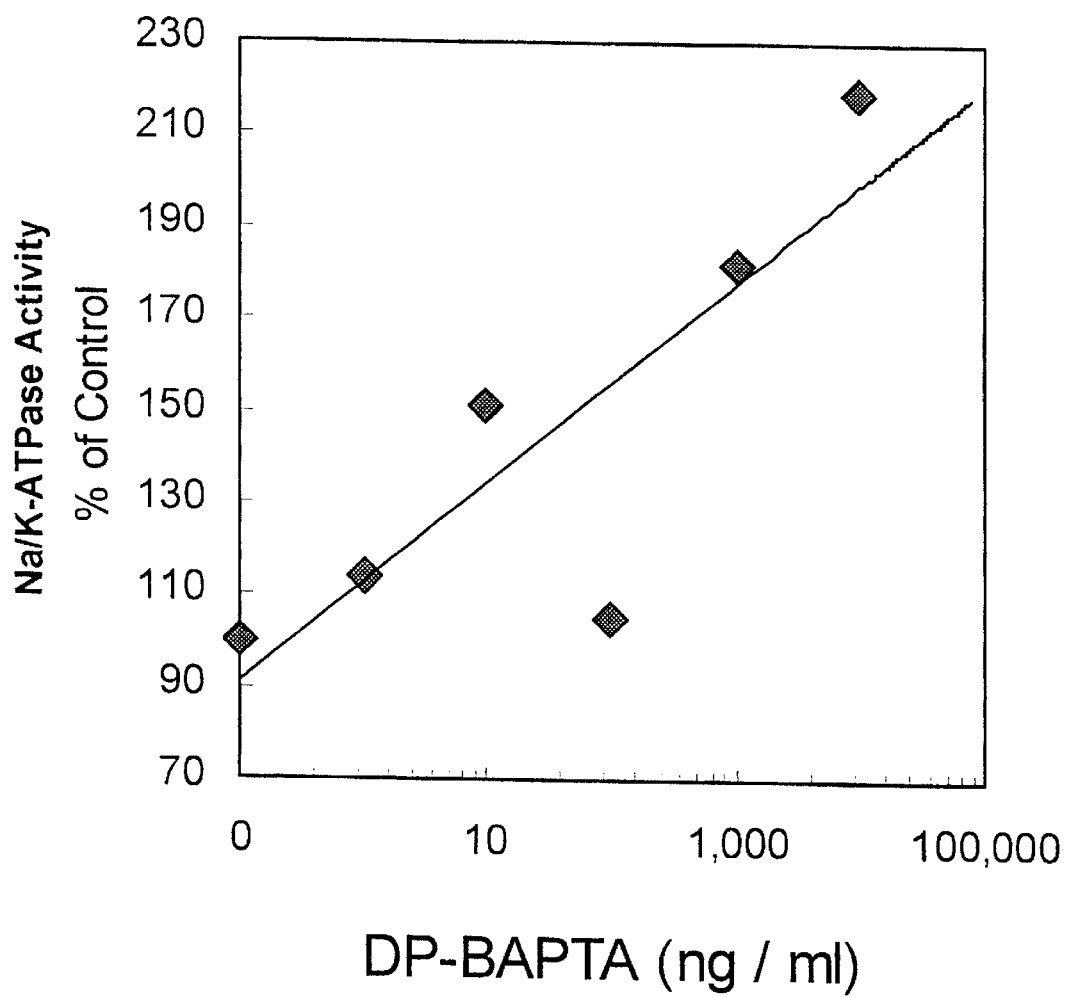
FIG. 4 depicts Na/K-ATPase activity (as % of control without drugs) measured in mouse cortex homogenate in the presence of different concentrations of diethyl ester of BAPTA (DP-BAPTA-27).

As shown in FIG. 4, DP-BAPTA 27 induced a dose dependent increase in Na/K-ATPase activity in the mouse cerebral cortex, therefore, under physiological conditions, conceivably resulting in a lower levels of extracellular $K^+$.

Example 7
Effects of BAPTA-diesters on Cellular Cardiac Function

The cardioprotective efficacy of diethyl-BAPTA (DP-BAPTA-23) was appraised by investigating the effect of this drug on the membrane action potential in cultured cardiomyocytes.

Ventricular myocytes were obtained from adult guinea pig (350–400 gr) by an enzymatic dissociation procedure (Isenberg G. and Klockner U. (1982) Pflugers Arch 395, 6–18). The cells were mounted on the stage of an inverted microscope (Nikon, DIAPHOT-TMD, Tokyo, Japan) in 0.5 ml recording bath. The bath was superfused with Tyrode's solution (140 mM NaCl, 4 mM KCl, 1.8 mM $CaCl_2$, 1 mM $MgCl_2$, 10 mM glucose and 5 mM HEPES, pH 7.4) at a rate of 1–2 ml/min. Myocytes were stimulated at 0.2 Hz and studied at room temperature (24–25° C.). Patch electrodes were prepared from glass micropipettes and had a tip resistance of 2–4 MΩ when filled with the pipette solution containing 120 mM K-aspartate, 20 mM KCl, 3.5 mM $MgCl_2$, 20 mM $KH_2PO_4$, 3 mM $Na_2ATP$, 10 mM glucose and 1 mM EGTA pH 7.4.

Action potentials were recorded from the guinea pig ventricular myocytes by means of Axon 200A (Axon Instruments, Inc. Foster City, Calif., USA), as previously described (Felzen et al. 1995, Pflugers Arch: 427, 422–431; Felzen et al. 1996, Circ. Res. 78, 253–261).

It was found that $10^{-11}$–$10^{-14}$ mol/L DP-BAPTA 23 induces hyperpolarization by decreasing (8 mV) the resting potentials of the cultured cardiomyocytes, and shortening their action potential duration (results not shown).

Figure 5:
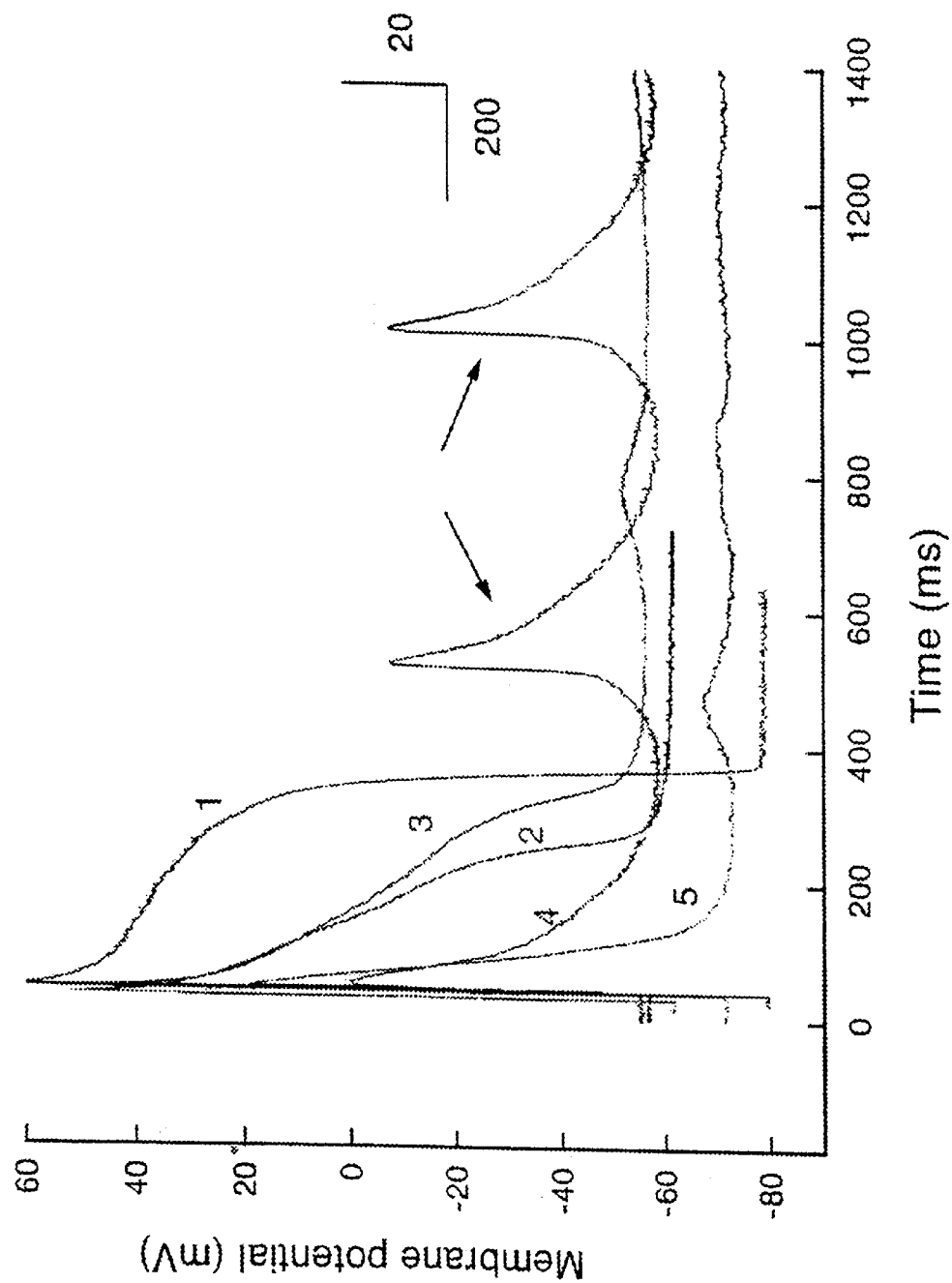
FIG. 5 depicts membrane action potential in stimulated cultured cardiomyocytes pre-incubated as follows: 1-control, no addition; 2-ouabain $10^{-6}$ M, 6 min., 3-ouabain $10^{-6}$ M, 10 min.; 4-ouabain $10^{-6}$ M, 13 min.; 5-ouabain $10^{-6}$ M+DP-BAPTA-23 $10^{-10}$ mg/ml, 35 min.

In FIG. 5 are shown the membrane potential measurements from stimulated myocytes incubated in the absence (trace 1, control cells) or presence of $10^{-6}$ M ouabain for 6 min (trace 2), 10 min (trace 3) and 13 min (trace 4) in comparison to the membrane potential measured from stimulated myocytes incubated with ouabain and $10^{-10}$ mg/ml DP-BAPTA 23 for 35 min (trace 5).

As can be seen in FIG. 5, incubation for 13 min with the Na/K-ATPase inhibitor, ouabain, induced a delayed after depolarizations (DAD) in the cardiomyocytes (marked with arrows on trace 4). This response, characterizing ouabain toxicity, was abolished by DP-BAPTA 23 (trace 5).

Example 8
Effects of BAPTA Diesters on Glutamate Induced Neuronal Cell Death

The neuropotective potential of BAPTA diesters of the invention were evaluated in the in vitro model system of glutamate toxicity.

Neonatal cortical neurons from rat were plated in 24 well plates and grown in a tissue culture as described in Sattler et al. (J. Cereb Blood Flow Metab, 17, 456 (1997))

Cells were washed once with 0.5 ml/well of Control Solution to remove any serum proteins. The Control Solution contained: 121 mM NaCl, 5 mM KCl, 10 mM HEPES acid, 7 mM HEPES-Na Salt, 1 mM Na-pyruvate, 1.8 mM CaCl, 3 mM $NaHCO_3$, 0.01 mM glycine, 20 mM D-Glucose, pH 7.4 (Sigma). DP-BAPTA-23 was first dissolved in DMSO and further diluted in the control solution to concentrations of 300, 100, 30, 10 and 3 μM. The amount of DMSO added to the cells should not exceed 1%. The cultured neuronal cells were loaded with the tested DP-BAPTA-23 (0.5 ml/well) and were incubated for 1 hr at 37° C. in a humidified chamber. The medium in the plates was then aspirated and replaced with fresh control solution and incubated for further 30 min at 37° C. Propidium Iodide (PI) from 1 mg/ml stock solution (Molecular Probes Inc., Cat #P-1304) was added to each well at final concentration of 50 ug/ml and a baseline fluorescence reading was taken. The cells were then treated with 300 mM of L-glutamate (Sigma) for 1 hour at room temperature in the absence or presence of various concentrations of DP-BAPTA-23, as indicated in each experiment.

Figure 6:
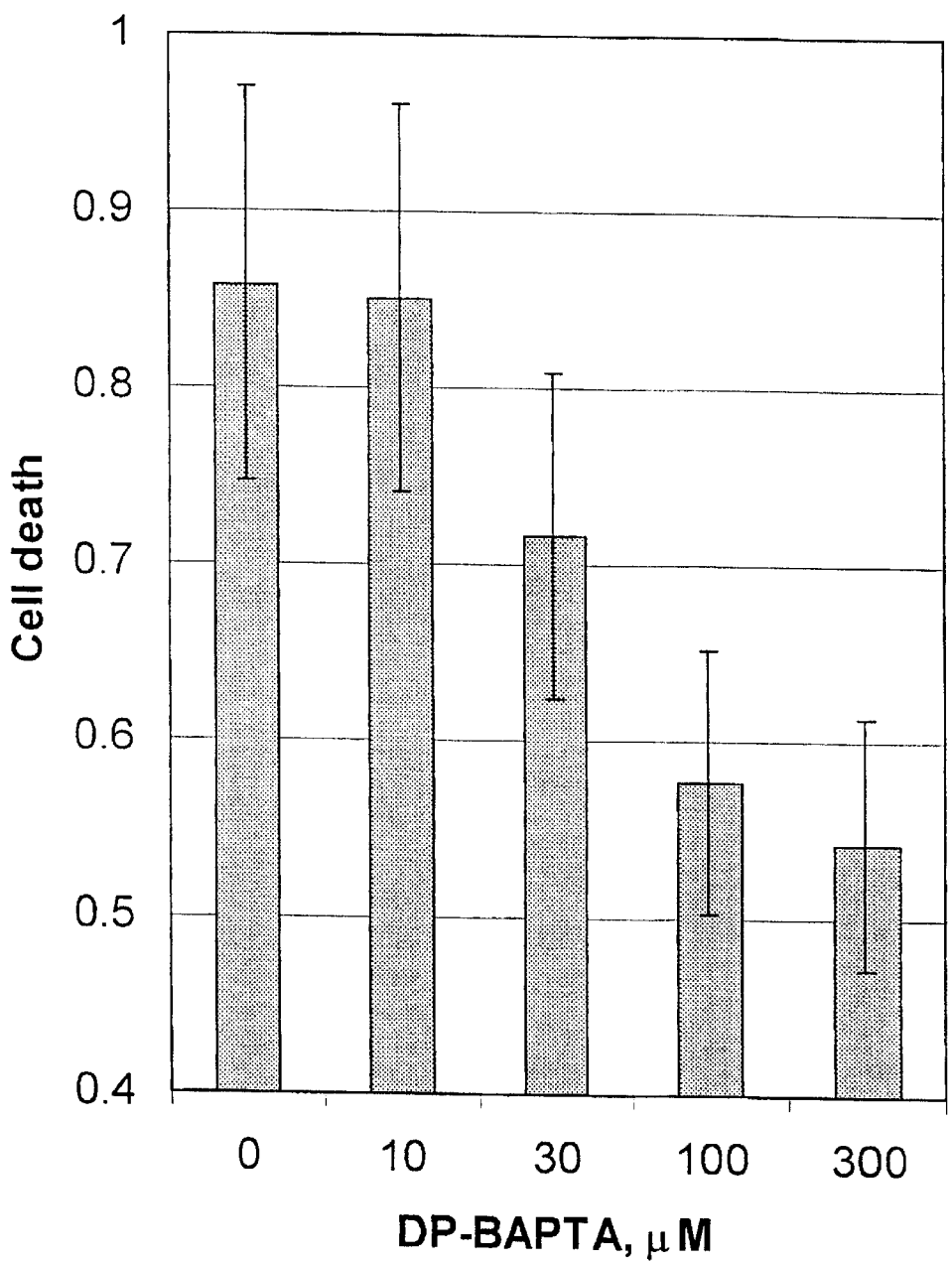
FIG. 6 depicts glutamate-induced cell death in the presence of different concentrations of DP-BAPTA-99 added 1 hour prior to the glutamate insult.

In the protocols wherever the cells were treated with the BAPTA-diester prior to the glutamate insult the drug was present in the medium throughout the insult period (FIG. 6). In other cases, DP-BAPTA was added only following the glutamate insult, at times as indicated (see FIG. 7).

Control solution without any glutamate was added to the control wells containing the tested BAPTA-diester, in order to check for the level of toxicity caused by the compound alone.

After the insult, the medium with glutamate was removed and changed for same medium without glutamate but containing PI (50 ug/ml). PI fluorescence measurements were taken at 1 hour intervals for 24 hours.

Background subtracted fluorescence measurements were normalized against PI fluorescence measurements taken from identical cultures exposed to 1 mM NMDA for 1 hour. Cell death was monitored by fluorescence readings in Cytofluor II Multi-well plate scanner (PerSeptive Biosystems). The glutamate insult produced close to 100% neuronal cell death within 24 hours.

The fraction of dead cells were calculated as follow:

Fraction dead=$(F_t-F_0)/F_{NMDA}$

Where $F_t$=PI Fluorescence at time t, $F_0$=Initial PI fluorescence at time zero, and $F_{NMDA}$=background subtracted PI fluorescence of identical cultures from the same dissection and plating, 24 hours after a 60 min exposure to 1 mM N-methyl-Daspartate (NMDA).

As shown in FIG. 6, DP-BAPTA-23 diminished glutamate-induced neuronal cell death in a dose dependent manner. This protective effect is evident at the BAPTA-diester concentration as low as 30 μM.

Figure 7:
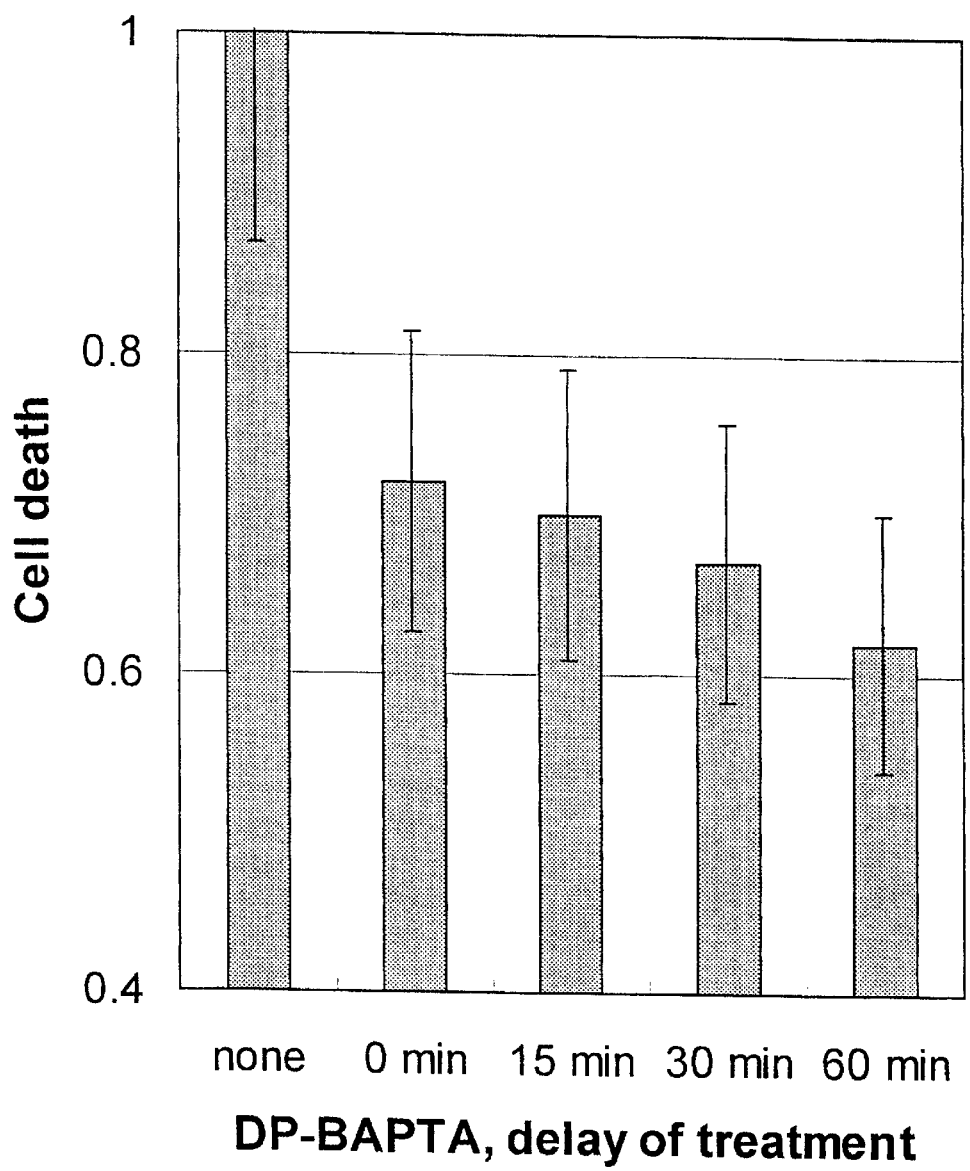
FIG. 7 depicts glutamate-induced cell death in the presence of DP-BAPTA-99 added at different times as indicated following glutamate insult.

Moreover, this neuroprotective effect was demonstrated when the DP-BAPTA (100 μM) was added either one hour prior to (FIG. 6), with Glu or up to 60 min after the glutamate insult (see FIG. 7)

Example 9
Neurorotective Effects of BAPTA-diesters—Global Forebrain Ischemic Model The neuropotective potency of BAPTA diesters of the invention was further examined in the global forebrain ischemic model system in Mongolian gerbils.

Animal. Male Mongolian gerbils 60–70 g (Charles River Laboratories, USA) were used for the study.

Induction of ischemia. Anesthesia was induced in gerbils with halothane (4%) in an anesthesia chamber (30% oxygen, 70% nitrous oxide) and was maintained with 1% halohtane in 30% oxygen and 70% nitrous oxide using face masks. For ischemia induction, both common carotid arteries were isolated via a neck midline incision and temporarily occluded for 10 or 20 min, as indicated, using arterial clips. During the entire period of cerebral ischemia, when the clips were in place, anesthesia was maintained only with 30% oxygen and 70% nitrous oxide, without halothane. Rectal temperature, monitored with a rectal probe, was maintained throughout ischemia at 37–37.5° C. by using a warming lamp and heating pad. Whenever applied, the tested BAPTA diesters were administered to the animals either parenterally via i.p. or orally, at the times and dosages as indicated in each particular experiment. Control animals were treated with the vehicle alone, i.e with 0.9% NaCl solution instead of the PABTA diester compound.

Viability studies. Animal survival following 20 min period of global forebrain ischemia was monitored up to 10 days after ischemia.

Statistics. Statistical analysis was carried out using the Student's t-test with Bonferroni corrections and $p<0.05$ as the level of significance.

Neuronal-specific enolase (NSE) assay. Blood samples were taken from the orbital sinus of gerbils 24 and 72 hours after 10 min period of cerebral ischemia. Blood samples were centrifuged for 5 min at 3000 rpm to obtain serum (the supernatant fraction). NSE activity in the serum was determined by radioimmunoassay using NSE kit (Pharmatope Ltd.,Israel).

The enzymatic activity of neuronal-specific enolase (NSE ) in the serum was used for evaluating the efficacy of the tested BAPTA-diesters in preventing neuronal damage. It was found that in experimental global ischemia, NSE levels are increased in serum from 2 to 192 hours succeeding the ischemia which corresponded to the delayed neuronal cell death occurring under these experimental conditions. Thus, NSE may serve as a quantitative marker for the degree of neuronal damage.

Figure 8:
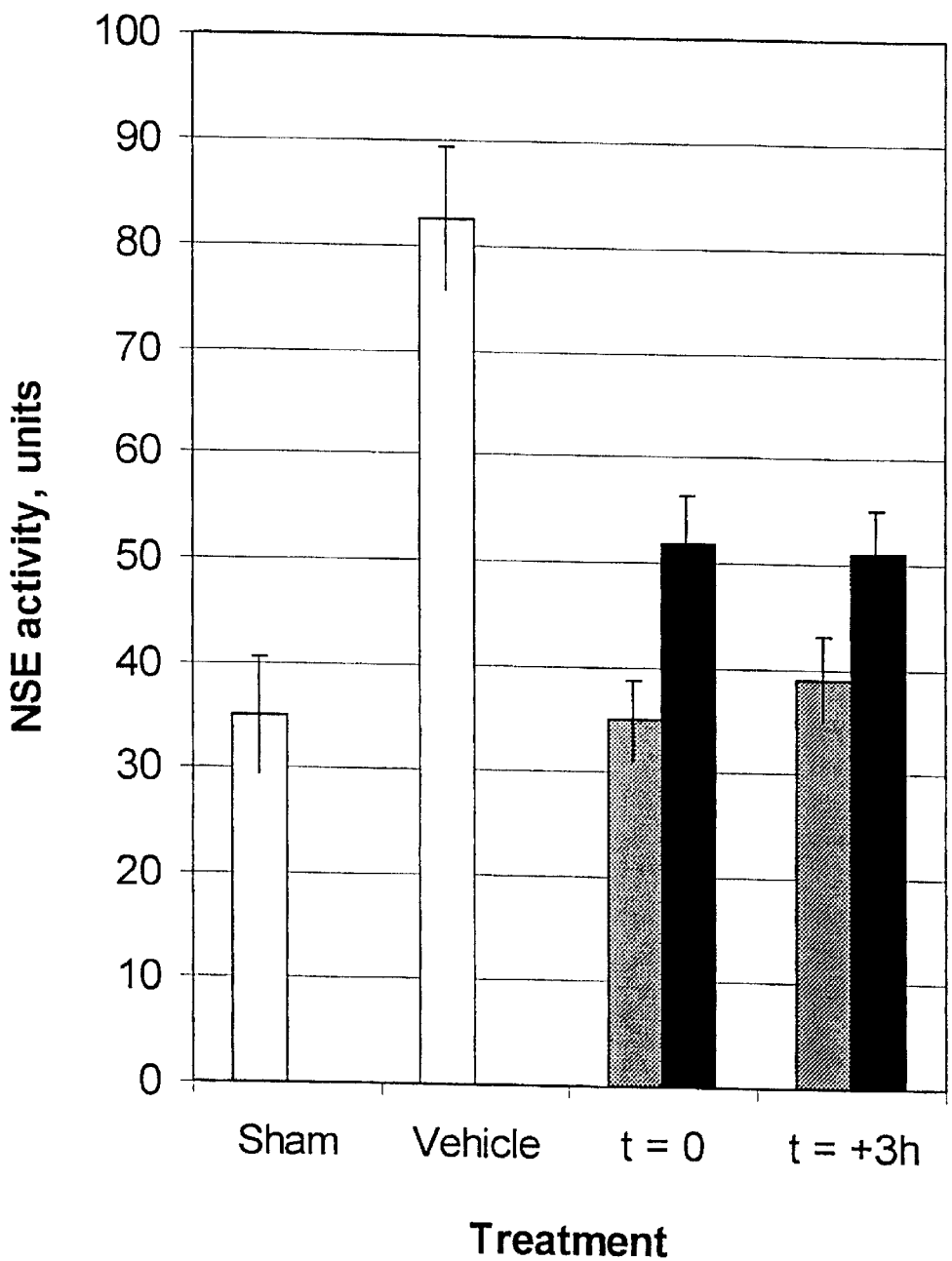
FIG. 8 depicts neuronal specific enolase (NSE) activity measured in the serum of Mongolian gerbils 24 hours following global forebrain ischemia, as a function of their treatment. t=0 and t=+3 h represent the time, in hours, relative to the onset of reperfusion, when dioctyl ester of BAPTA (DP-BAPTA-60, gray bars) and dioctyl-ethylene glycol ester of BAPTA (DP-BAPTA-99, dark bars) were administered i.p.
Figure 9A:
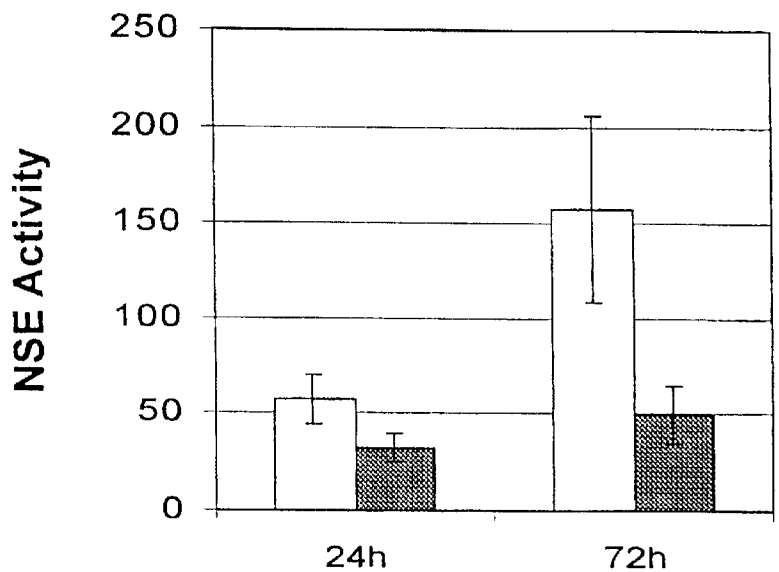
FIGS. 9A–B depict neuronal specific enolase (NSE) activity measured in the serum of Mongolian gerbils 24 and 72 hours following global forebrain ischemia. DP-BAPTA-99 (dark bars) was orally administered in two schemes (A) 0.5 mg/kg dose at 4 hours before the onset of reperfusion followed by another 0.5 mg/kg dose at the beginning of reperfusion, and (B) 0.5 mg/kg daily for 3 days after ischemia. NSE activity in control animals treated with vehicle solution are presented in light bars.
Figure 9B:
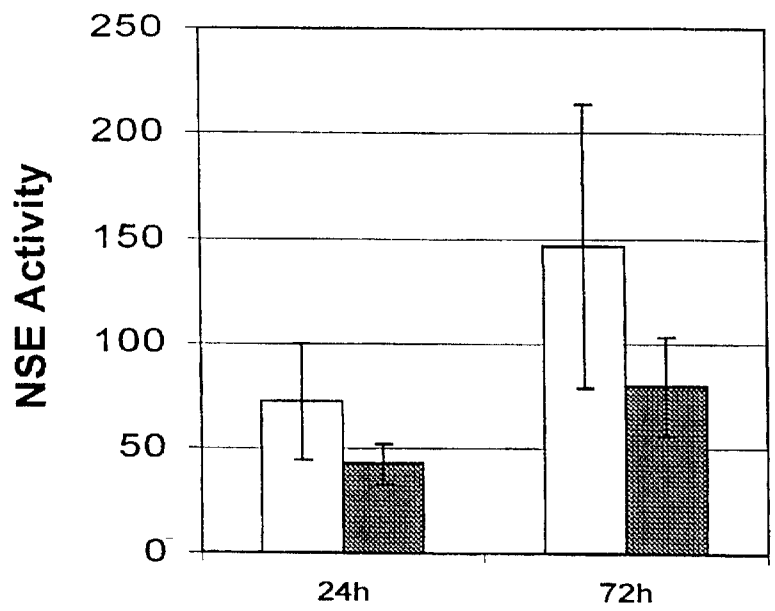
Figure 10:
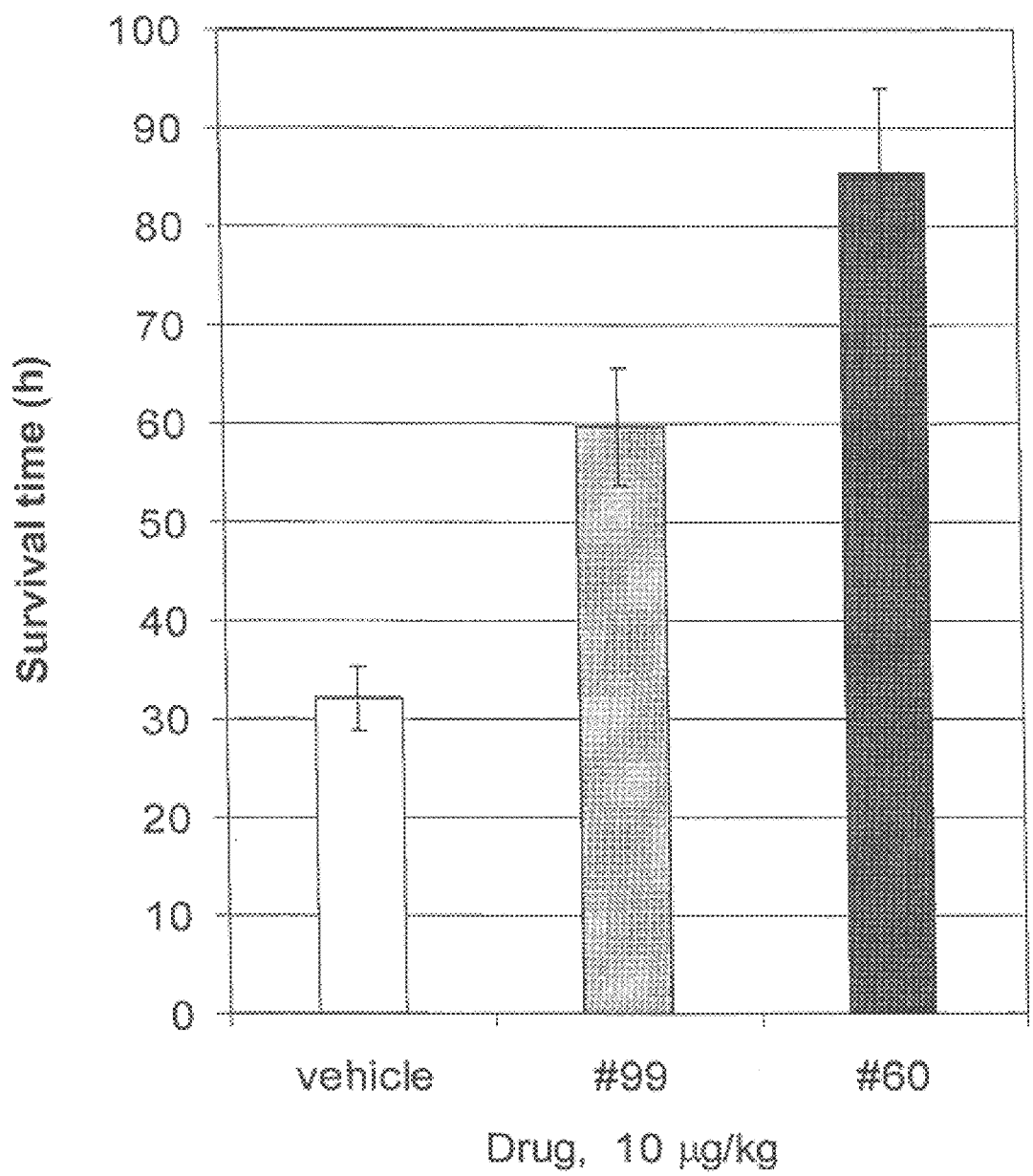
FIG. 10 depicts survival time, in hours, of Mongolian gerbils following 20 min of global forebrain ischemia. The animals received either vehicle solution (light bar) or 10 µg/kg of DP-BAPTA-60 (gray bars) or DP-BAPTA-99 (dark bars) administered i.p. in a single dose at the onset of reperfusion.

In FIGS. 8, 9 and 10 are summarized results of experiments wherein two BAPTA diesters of the invention, dioctyl-BAPTA (DP-BAPTA-60, disodium salt) and dioctyl-ethylene glycol-BAPTA (DP-BAPTA-99, disodium salt), were tested for their neuronal protective effects. Different regimen and administration routes of the drug were examined in the model system of global forebrain ischemia in M. Gerbils. The parameters followed were (i) the activity of the neuronal-specific enolase in the animal's serum as an indicator for neuronal cell death (FIGS. 8 & 9) and (ii) animal survival (FIG. 10).

As shown in FIG. 8, a single dose of 5μg/kg of either DP-BAPTA-60 (gray bars) or DP-BAPTA-99 (black bars) administered i.p. to the ischemic gerbils immediately at the onset of reperfusion (t=0) or 3 hours after the beginning of reperfusion (t=3) prevented neuronal damage. These results indicate that DP-BAPTA drugs act in both curative and preventing modes.

In FIG. 9 is shown the neuroprotective effect of DP-BAPTA 99 administered orally in two schemes: a) 0.5 mg/kg dose at 4 hours before the onset of reperfusion followed by another 0.5 mg/kg dose at the beginning of reperfusion, and b) 0.5 mg/kg daily for 3 days after ischemia. In both regimens, DP-BAPTA 99 exhibits a strong protective effect demonstrated by the significant reduction in NSE activity in the serum, measured 24 h and 72 h after global cerebral ischemia.

In another experiment, the protective effect of BAPTA-diesters was evaluated by monitoring the survival time of gerbils subjected to 20 min of global forebrain ischemia, as described above. The tested animals (N=15 in each group) received either 10 μg/kg of DP-PABTA-60 or DP-PABTA-99 administered i.p. in a single dose at the onset of reperfusion. Control animals (N=30) received the vehicle solution.

As shown in FIG. 10, both DP-PABTA-60 and DP-PABTA-99 extended the survival of the animals, by 2- and 3-fold, respectively.

In conclusion, it was demonstrated that BAPTA diesters are effective in both curative and preventing modes in protecting against neural damage caused by ischemia, and that parenteral as well as oral routes for administration of the drug are practical.

It is important to note that both the disodium and calcium salts of dioctyl-BAPTA were equally effective in their neuroprotective capacities. On the other hand, in this model system, the sodium salt of dioctyl-ethylene glycol-BAPTA (DP-BAPTA-99) showed much pronounced neuroprotective activity comparing to the calcium salt of the molecule.

Example 10
Histopathology Analysis of Neurorotective Effects of BAPTA-diesters

In order to further establish the neuroprotective activity of BAPTA-diesters, a detailed semi-quantitative microscopic pathology analysis was conducted on brain samples of animals subjected to induction of global forebrain ischemia, performed either in the absence or presence of a BAPTA-diester.

Two of the currently most neuroprotectively potent BAPTA-diesters of the invention were tested, i.e. dioctyl-BAPTA (DP-BAPTA 60) and dioctyl-ethylene glycol-BAPTA (DP-BAPTA 99), both disodium salts.

Thirty nine Mongolian Gerbils were exposed to 10 minutes of global forebrain ischemia induced according to the procedure described in Example 9. The animals were divided to three groups that were treated as follows:

Group I: 13 Gerbils; injected, i.p. with a single dose of 5 μg DP-BAPTA 60 /kg body weight immediately after ischemia.

Group II: 11 Gerbils; injected, i.p. with a single dose of 5 μg DP-BAPTA 99 /kg body weight immediately after ischemia.

Group III: 15 Gerbils; control animals injected with the vehicle, i.e. saline solution.

Three days after ischemia, the animals were re-anaesthetized with ketamine and ksilazyne, their brains were surgically removed and were stored in 4% formalin in PBS for 7 days. Slides, 7 μm thick, were taken from the area of the dorsal hippocampus and were stained with hematoxylin and eosin for microscopic examination.

The CA-1, CA-2, CA-3 and dentate gyrus sub-fields of the hippocampus were evaluated when divided to three sub-areas: medial, middle and lateral. The total number of live cells from each section was then counted and neuronal damage was estimated. The arbitrary scale used for brain damage evaluation include five stages: 0—denotes normal tissue, no damage; 1—denotes minimal damage, less than around 20% necrosis of neurons; 2—denotes mild damage, less than around 40% necrosis of neurons; 3—denotes moderate damage, less than around 60% necrosis of neurons; and 4—denotes marked damage, more than 80% of neurons are dead.

Figure 11:
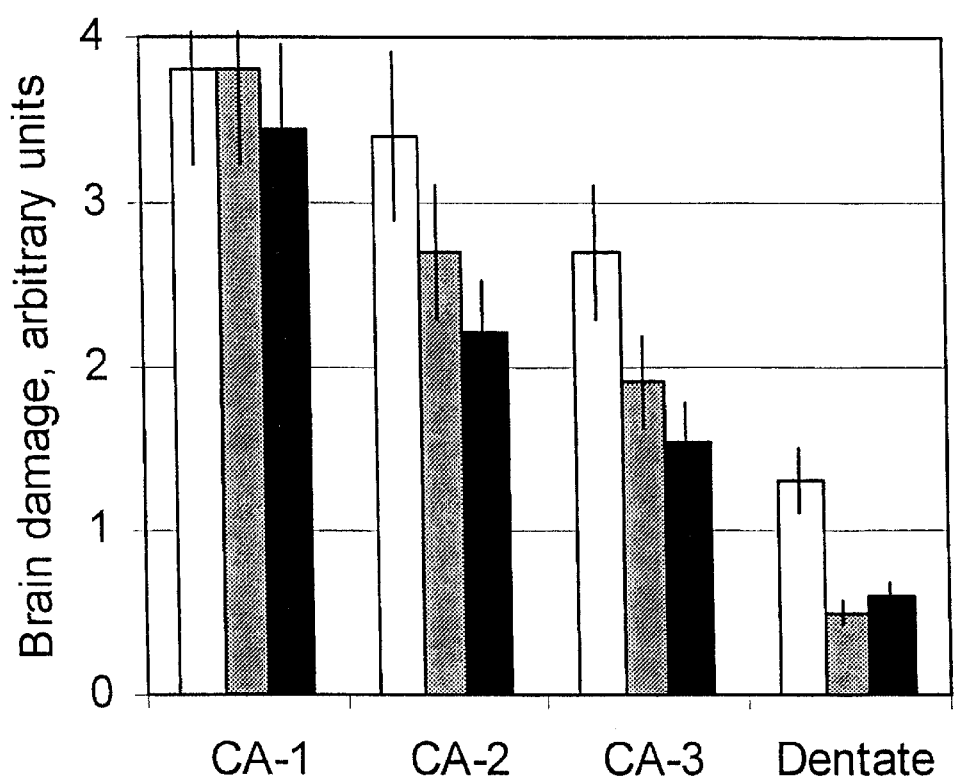
FIG. 11 depicts an histopathology analysis of ischemic-induced brain damage (0=normal; 1=minimal; 2=mild; 3=moderate; 4=marked) in different regions of the hippocampus (CA-1, CA-2, CA-3 and Dentate gyrus) in gerbils treated with DP-BAPTA-60 (gray bars), DP-BAPTA-99 (dark bars) or saline solution (vehicle, light bar).

As can be seen in FIG. 11, DP-BAPTA 99 demonstrates a significant neuroprotective effect in the CA-2, CA-3 and dentate gyrus regions of the hippocampus. DP-BAPTA 60 was also found effective in decreasing the ischemia-induced neuronal damage in the same regions, albeit to a lesser extent than DP-BAPTA 99.

Example 11
Anti-epileptic Effect of BAPTA-diesters (in vivo Model)

The anti-epileptic activity of DP-BAPTA-99 was followed in the animal model of Wistar rats, where seizures were induced by Pilocarpine (400 mg/kg).

Wistar rats weighing approximately 350 gr were used for this experiment. DP-BAPTA-99, at different concentrations as indicated in FIGS. 12A-B, was injected i.p. one hour before the injection of pilocarpine. Meythyl scopolamine (1 mg/kg) was injected s.c. 30 min pre-pilocarpine (400mg/kg, i.p.) in order to reduce peripheral muscarinic effects of pilocarpine.

Following injection of pilocarpine, within minutes, animals exhibit release of porfin from around the eyes, chronic mastication, nodding, myoclonic jerks, and wet dog shakes. These are all stages of limbic seizures, comparable to stages 1–2 of the Racine scale. The animals then usually move on to stage 3, which involves forelimb-drumming activity. Usually within 20 min, animals exhibit signs of seizure generalization. This includes rearing, or rearing and falling with concurrent forelimb clonus activity and generalized clonic seizures. Usually within 30 min, the rats are in status epilepticus. The status is limbic in nature, punctuated by brief episodes of clonic seizures. Status epilepticus is a seizure that does not stop spontaneously. In the rat model, this means that it continues for over 5 min. After the animals were in status epilepticus for 3 hours (and only those in status), the seizures were stopped by the administration, i p., of 10 mg/kg diazepan and Phenytoin (60 mg/kg). Mortality during status period with the high-dose pilocarpine model is usually around 30–50%.

Figure 12:
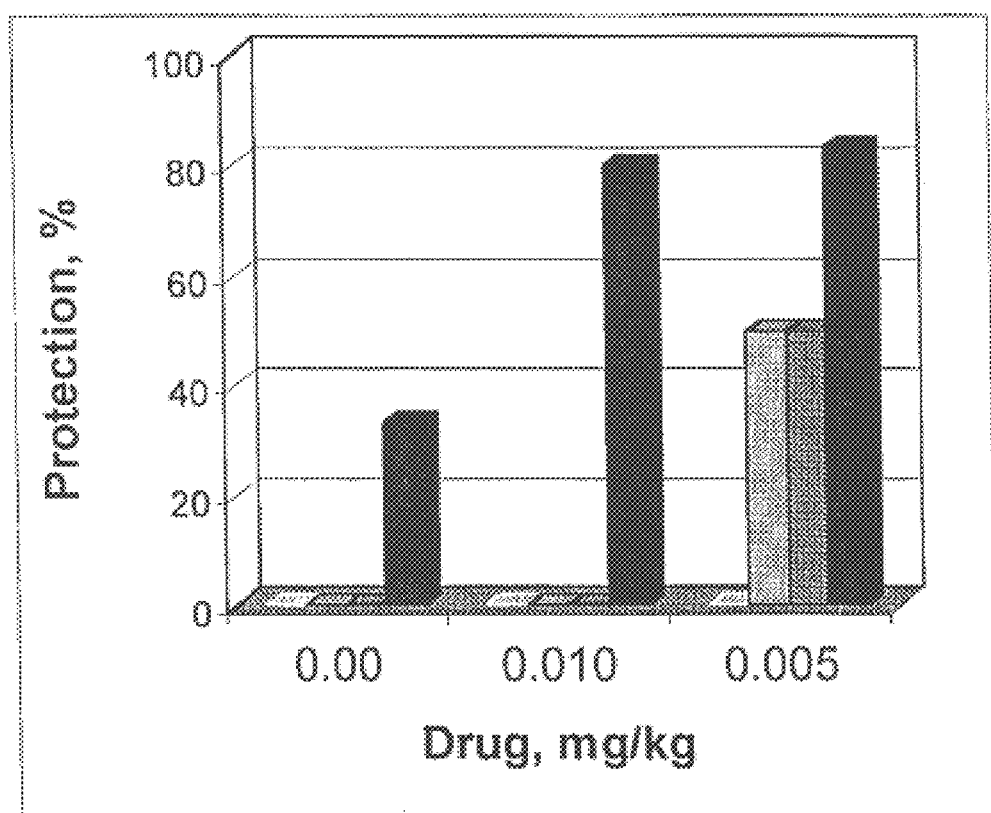
FIG. 12 depicts anti-epileptic protection effect (%) of different concentrations of DP-BAPTA-99 in the animal model of Wistar rats wherein epilepsy was induced by Pilocarpine, 400 mg/kg. The epilepsy symptoms monitored were: Limbic seizures (white); General Seizures (light gray), L-SE (dark gray) and survival (black).

As shown in FIG. 12, DP-BAPTA-99 has no effect on limbic seizures, but is capable of preventing generalized seizures, and prevents status epilepticus in about half of the population. In addition, the drug reduces mortality that occurs during the 3 hour period of status epilepticus.

Thus, it can be concluded that DP-BAPTA-99 can prevent the spread (generalization) of seizures.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A method for treating a disease or disorder related to an excess of divalent metal ions, comprising administering to an individual in need thereof a therapeutically effective amount of a stable lipophilic diester of a pharmaceutically acceptable chelating agent for divalent metal ions.

2. A method for treating a disease or disorder related to an excess of intracellular $Ca^{++}$ ions, comprising administering to an individual in need thereof a therapeutically effective amount of a stable lipophilic diester of a pharmaceutically acceptable calcium chelating agent.

3. The method according to claim 2, wherein said lipophilic diester comprises a chelating agent (a) with alcohol (b), where (a) is a pharmaceutically acceptable chelating agent for calcium having the formula (HOOC—$CH_2$—)$_2$—N—A—N—(—$CH_2$COOH)$_2$ where A is saturated or unsaturated, aliphatic, aromatic or heterocyclic linking radical containing, in a direct chain link between the two depicted nitrogen atoms, 2–8 carbon atoms in a continuous chain which is interrupted by 2–4 oxygen atoms, provided that the chain members directly connected to the two depicted nitrogen atoms are not oxygen atoms, and (b) is a pharmaceutically acceptable alcohol selected from the group of straight chain or branched, saturated or unsaturated alkyl, aminoalkyl, and substituted or unsubstituted arylalkyl radicals; and pharmaceutically acceptable salts of said di-esterified carboxylic acids.

4. The method according to claim 3, wherein said linking radical A is a member selected from the group consisting of saturated or unsaturated aliphatic chain interrupted by 2–4 oxygen atoms, and —CR═CR—O—$CH_2CH_2$—O—CR'═CR'—, where each of the pairs of radicals R—R and R'—R', together with the attached —C═C— moiety, complete an aromatic or heterocyclic ring containing 5 or 6 ring atoms, the ring completed by R—R being the same as or different from the ring completed by R'—R'.

5. The method according to claim 3, wherein said linking radical A is —$CH_2CH_2$—O—$CH_2CH_2$—O—$CH_2CH_2$—.

6. The method according to claim 3, wherein said linking radical is —CR═CR—O—$CH_2CH_2$—O—CR'═CR'—, where each of the pairs of radicals R—R and R'—R', together with the attached —C═C— moiety, complete an aromatic or heterocyclic ring which is selected from the group consisting of furan, thiophene, pyrrole, pyrazole, imidazole, 1,2,3-triazole, oxazole, isoxazole, 1,2,3-oxadiazole, 1,2,5-oxadiazole, thiazole, isothiazole, 1,2,3-thiadiazole, 1,2,5-thiadiazole, benzene, pyridine, pyridazine, pyrimidine, pyrazine, 1,2,3-triazine, 1,2,4-triazine, and 1,2-, 1,3- and 1,4-oxazines and -thiazines, the ring completed by R—R being the same as or different from the ring completed by R'—R'.

7. The method according to claim 3, wherein the linking radical A is —CR═CR—O—$CH_2CH_2$—O—CR'═CR'—, where each of the pairs of radicals R—R and R'—R', together with the attached —C═C— moiety, completes the same or different rings selected from unsubstituted and substituted benzene rings, in which substituted benzene rings contain 1–4 substituents selected from the group consisting of saturated or unsaturated $C_{1-4}$-alkyl, saturated or unsaturated $C_{1-4}$-alkoxy, fluorine, chlorine, bromine, iodine and $CF_3$, or a single divalent substituent which is —O—$(CH_2)_n$—O— and n=1–3.

8. The method according to claim 3 wherein said chelating agent is selected from ethylene-1,2,-diol-bis-(2-aminoethyl ether)-N,N,N',N'-tetraacetic acid and 1,2-bis-(2-aminophenoxy)ethane-N,N,N',N'-tetraacetic acid.

9. The method according to claim 3, wherein the diester of a chelating agent is a compound of the general formula I:

Formula 1 wherein the substituents on the aromatic rings are in the ortho position, R is selected from the group consisting of $C_nH_{2n+1}$ (n=1–10), $C_nH_{2n+1}(OCH_2CH_2)_m$ (n=1–20, m=1–6), $(C_nH_{2n+1})_2N(CH_2)_m$(n=1–6, m=1–6) and substituted or unsubstituted $ArCH_2$; and M denotes any physiologically acceptable cation.

10. The method according to claim 9 wherein the R is a monoalkyl ether of mono- di and tri- ethylene glycol.

11. The method according to claim 9 wherein R is selected from the group consisting of $C_2H_5$, $C_3H_7$, i-$C_3H_7$, $C_4H_9$, $C_7H_{15}$, $C_8H_{17}$, $CH_2C_6H_5$, $CH_3OCH_2CH_2$, $C_2H_5OCH_2CH_2$, $C_3H_7OCH_2CH_2$, $C_4H_9OCH_2CH_2$, $C_7H_{15}OCH_2CH_2$, $C_8H_{17}OCH_2CH_2$, $C_{10}H_{21}OCH_2CH_2$, $C_{16}H_{33}OCH_2CH_2$, $C_{18}H_{37}OCH_2CH_2$, $CH_3(OCH_2CH_2)_2$, $C_2H_5(OCH_2CH_2)_2$, $C_4H_9(OCH_2CH_2)_2$, $C_6H_{13}(OCH_2CH_2)_2$, $C_7H_{15}(OCH_2CH_2)_2$, $C_8H_{17}(OCH_2CH_2)_2$, $C_{10}H_{21}(OCH_2CH_2)_2$, $CH_3(OCH_2CH_2)_3$, $(CH_3)_2NCH_2CH_2$, $C_7H_{15}(OCH_2CH_2)_3$.

12. The method according to claim 9 wherein R is selected from the group consisting of $C_2H_5$, $C_3H_7$, $C_4H_9$, $C_7H_{15}$, $C_8H_{17}$, $C_8H_{17}OCH_2CH_2$, $C_{10}H_{21}OCH_2CH_2$, $C_{16}H_{33}OCH_2CH_2$, $C_{18}H_{37}OCH_2CH_2$, $C_8H_{17}(OCH_2CH_2)_2$, $C_{10}H_{21}(OCH_2CH_2)_2$.

13. The method according to claim 12 wherein R is $C_8H_{17}$.

14. The method according to claim 12 wherein R is $C_8H_{17}OCH_2CH_2$.

15. The method according to any one of claims 2 to 14 wherein said disease or disorder related to an excess of intracellular $Ca^{++}$ ions is selected from the group consisting of brain and cardiac ischemia, stroke, myocardial infarction, epilepsy, Alzheimer's disease, Parkinson's disease, acute inflammation, urinary incontinence, prostatic hypertrophy, muscular spasm, arterial hypertension, asthma and irritable bowel syndrome.

16. The method according to any one of claims 2 to 14, wherein said disease or disorder related to an excess of intracellular $Ca^{++}$ ions is brain or cardiac ischemia, stroke, epilepsy, Alzheimer's disease or cardiac arrhythmia.

17. A stable di-esterified carboxylic acid (a) with hydroxy compound (b), where (a) is a pharmaceutically acceptable chelating agent for divalent metal ions having the formula $(HOOC—CH_2—)_2—N—A—N—(—CH_2COOH)_2$ wherein A is saturated or unsaturated, aliphatic, aromatic or heterocyclic linking radical containing, in a direct chain link between the two depicted nitrogen atoms, 2–8 carbon atoms in a continuous chain which is interrupted by 2–4 oxygen atoms, provided that the chain members directly connected to the two depicted nitrogen atoms are not oxygen atoms, and (b) is a pharmaceutically acceptable alcohol selected from the group of straight chain or branched, saturated or unsaturated alkyl, aminoalkyl and substituted or unsubstituted arylalkyl radicals; and pharmaceutically acceptable salts of said di-esterified carboxylic acids.

18. The diester according to claim 17, wherein said linking radical A is selected from the group consisting of saturated or unsaturated aliphatic chain interrupted by 2–4 oxygen atoms, and —CR=CR—O—CH$_2$CH$_2$—O—CR'=CR'—, where each of the pairs of radicals R—R and R'R', together with the attached —C=C— moiety, complete an aromatic or heterocyclic ring containing 5 or 6 ring atoms, the ring completed by R—R being the same as or different from the ring completed by R'—R'.

19. The diester according to claim 18, wherein said linking radical A is —CH$_2$CH$_2$—O—CH$_2$CH$_2$—O—CH$_2$CH$_2$—.

20. The diester according to claim 18, wherein said linking radical is —CR=CR—O—CH$_2$CH$_2$—O—CR'=CR'—, where each of the pairs of radicals R—R and R'—R', together with the attached —C=C— moiety, complete an aromatic or heterocyclic ring which is selected from the group consisting of furan, thiophene, pyrrole, pyrazole, imidazole, 1,2,3-triazole, oxazole, isoxazole, 1,2,3-oxadiazole, 1,2,5-oxadiazole, thiazole, isothiazole, 1,2,3-thiadiazole, 1,2,5-thiadiazole, benzene, pyridine, pyridazine, pyrimidine, pyrazine, 1,2,3-triazine, 1,2,4-triazine, and 1,2-, 1,3- and 1,4-oxazines and -thiazines, the ring completed by R—R being the same as or different from the ring completed by R'—R'.

21. The diester according to claim 20, wherein the linking radical A is —CR=CR—O—CH$_2$CH$_2$—O—CR'=CR'—, where each of the pairs of radicals R—R and R'—R', together with the attached —C=C— moiety, completes the same or different rings selected from unsubstituted and substituted benzene rings, in which substituted benzene rings contain 1–4 substituents selected from the group consisting of saturated or unsaturated $C_{1-4}$-alkyl, saturated or unsaturated $C_{1-4}$-alkoxy, fluorine, chlorine, bromine, iodine and $CF_3$, or a single divalent substituent which is —O—$(CH_2)_n$—O— and n=1–3.

22. The diester according to claim 18, wherein said chelating agent is selected from ethylene-1,2-diol-bis-(2-aminoethyl ether)-N,N,N',N'-tetraacetic acid and 1,2-bis-(2-aminophenoxy)ethane-N,N,N'N'-tetraacetic acid.

23. A compound of the general formula I:

Formula 1 wherein the substituents on the aromatic rings are in the ortho position; R is selected from the group consisting of $C_nH_{2n+1}$(n=1–10), $C_nH_{2n+1}(OCH_2CH_2)_m$ (n=1–20, m=1–6), $(C_nH_{2n+1})_2N(CH_2)_m$(n=1–6, m=1–6) and substituted or unsubstituted $ArCH_2$; and M denotes any physiologically acceptable cation.

24. The compound of claim 23 wherein R is a monoalkyl ether of mono-,di-, or tri-ethylene glycol.

25. The compound according to claim 23 wherein R is selected from the group consisting of: $C_2H_5$, $C_3H_7$, i-$C_3H_7$, $C_4H_9$, $C_7H_{15}$, $C_8H_{17}$, $CH_2C_6H_5$, $CH_3OCH_2CH_2$, $C_2H_5OCH_2CH_2$, $C_3H_7OCH_2CH_2$, $C_4H_9OCH_2CH_2$, $C_7H_{15}OCH_2CH_2$, $C_8H_{17}OCH_2CH_2$, $C_{10}H_{21}OCH_2CH_2$, $C_{16}H_{33}OCH_2CH_2$, $C_{18}H_{37}OCH_2CH_2$, $CH_3(OCH_2CH_2)_2$, $C_2H_5(OCH_2CH_2)_2$, $C_4H_9(OCH_2CH_2)_2$, $C_6H_{13}(OCH_2CH_2)_2$, $C_7H_{15}(OCH_2CH_2)_2$, $C_8H_{17}(OCH_2CH_2)_2$, $C_{10}H_{21}(OCH_2CH_2)_2$, $CH_3(OCH_2CH_2)_3$, $(CH_3)_2NCH_2CH_2$ and $C_7H_{15}(OCH_2CH_2)_3$.

26. The compound according to claim 25 wherein R is selected from the group consisting of: $C_2H_5$, $C_3H_7$, $C_4H_9$, $C_7H_{15}$, $C_8H_{17}$, $C_8H_{17}OCH_2CH_2$, $C_{10}H_{21}OCH_2CH_2$, $C_{16}H_{33}OCH_2CH_2$, $C_{18}H_{37}OCH_2CH_2$, $C_8H_{17}(OCH_2CH_2)_2$ and $C_{10}H_{21}(OCH_2CH_2)_2$.

27. The compound according to claim 25 wherein R is $C_8H_{17}$.

28. The compound according to claim 25 wherein R is $C_8H_{17}OCH_2CH_2$.

29. A pharmaceutical composition comprising as an active ingredient a stable lipophilic diester of a chelating agent according to claim 17, and a pharmaceutically acceptable diluent or carrier.

30. The pharmaceutical composition according to claim 29 comprising as an active ingredient a compound of the general formula I:

Formula 1

wherein the substituents on the aromatic rings are in the ortho position; R is selected from the group consisting of $C_nH_{2n+1}$ (n=1–10), $C_nH_{2n+1}(OCH_2CH_2)_m$ (n=1–20, m=1–6), $(C_nH_{2n+1})_2N(CH_2)_m$ (n=1–6, m=1–6) and substituted or unsubstituted $ArCH_2$; and M denotes any physiologically acceptable cation.

31. The pharmaceutical composition according to claim 30 wherein said R is selected from the group consisting of: $C_2H_5$, $C_3H_7$, $C_4H_9$, $C_7H_{15}$, $C_8H_{17}$, $C_8H_{17}OCH_2CH_2$, $C_{10}H_{21}OCH_2CH_2$, $C_{16}H_{33}OCH_2CH_2$, $C_{18}H_{37}OCH_2CH_2$, $C_8H_{17}(OCH_2CH_2)_2$ and $C_{10}H_{21}(OCH_2CH_2)_2$.

32. The pharmaceutical composition according to claim 30 wherein R is $C_8H_{17}$.

33. The pharmaceutical composition according to claim 30 wherein R is $C_8H_{17}OCH_2CH_2$.

34. The pharmaceutical composition according to claim 31 for the treatment of a disease or a disorder related to an excess of divalent metal ions.

35. The pharmaceutical composition according to claim 34 for parenteral administration.

36. The pharmaceutical composition according to claim 34 for oral administration.

37. The pharmaceutical composition according to claim 34 wherein said divalent metal ions are selected from the group consisting of $Ca^{++}$, $Cd^{++}$, $Co^{++}$, $Cu^{++}$, $Fe^{++}$, $Hg^{++}$, $Mg^{++}$, $Mn^{++}$, $Pb^{++}$ and $Zn^{++}$, ions.

38. The pharmaceutical composition according to claim 34 wherein said disease or disorder is related to an elevated levels of intracellular $Ca^{++}$ ions.

39. The pharmaceutical composition according to claim 38 wherein said disease or disorder related to an excess of intracellular $Ca^{++}$ ions is selected from the group consisting of brain and cardiac ischemia, stroke, myocardial infarction, epilepsy, Alzheimer's disease, Parkinson's disease, acute inflammation, urinary incontinence, prostatic hypertrophy, muscular spasm, arterial hypertension, asthma and irritable bowel syndrome.

40. The pharmaceutical composition according to claim 39 wherein said disease or disorder related to an excess of intracellular $Ca^{++}$ ions is brain or cardiac ischemia, stroke, epilepsy, Alzheimer's disease or cardiac arrhythmia.

41. A method for the manufacture of a pharmaceutical composition, said method comprising:

combining a pharmaceutically effective amount of a composition comprising the diester according to claim 1 and a pharmaceutically acceptable diluent or carrier.

* * * * *

UNITED STATES PATENT AND TRADEMARK OFFICE
CERTIFICATE OF CORRECTION

PATENT NO. : 6,458,837 B1
APPLICATION NO. : 09/509393
DATED : October 1, 2002
INVENTOR(S) : Alexander Kozak et al.

Page 1 of 2

It is certified that error appears in the above-identified patent and that said Letters Patent is hereby corrected as shown below:

Col. 27 lines 1–14 should read,

9. The method according to claim 3, wherein the diester of a chelating agent is a compound of the general formula I:

Formula 1 wherein the substituents on the aromatic rings are in the ortho position, R is selected from the group consisting of $C_nH_{2n+1}$ (n=1-10), $C_nH_{2n+1}(OCH_2CH_2)_m$ (n=1-20, m=1-6), $(C_nH_{2n+1})_2N(CH_2)_m$ (n=1-6, m=1-6) and substituted or unsubstituted $ArCH_2$; and M denotes any physiologically acceptable cation.

UNITED STATES PATENT AND TRADEMARK OFFICE
CERTIFICATE OF CORRECTION

PATENT NO. : 6,458,837 B1
APPLICATION NO. : 09/509393
DATED : October 1, 2002
INVENTOR(S) : Alexander Kozak et al.

It is certified that error appears in the above-identified patent and that said Letters Patent is hereby corrected as shown below:

(Continued) Col. 23 lines 34–46, should read,

23. A compound of the general formula I:

Formula 1 wherein the substituents on the aromatic rings are in the ortho position, R is selected from the group consisting of $C_nH_{2n+1}$ (n=1-10), $C_nH_{2n+1}(OCH_2CH_2)_m$ (n=1-20, m=1-6), $(C_nH_{2n+1})_2N(CH_2)_m$ (n=1-6, m=1-6) and substituted or unsubstituted $ArCH_2$; and M denotes any physiologically acceptable cation.

Signed and Sealed this

Twenty-third Day of October, 2007

JON W. DUDAS
*Director of the United States Patent and Trademark Office*